US009039761B2

(12) United States Patent
Trogden et al.

(10) Patent No.: US 9,039,761 B2
(45) Date of Patent: May 26, 2015

(54) OCULAR IMPLANT DELIVERY ASSEMBLIES WITH DISTAL CAPS

(75) Inventors: John T. Trogden, Anaheim, CA (US); Robert T. Lyons, Laguna Hills, CA (US); James N. Chang, Newport Beach, CA (US); Michael R. Robinson, Irvine, CA (US); Werhner C. Orilla, Anaheim, CA (US)

(73) Assignee: Allergan, Inc., Irvine, CA (US)

( * ) Notice: Subject to any disclaimer, the term of this patent is extended or adjusted under 35 U.S.C. 154(b) by 626 days.

(21) Appl. No.: 11/552,630

(22) Filed: Oct. 25, 2006

(65) Prior Publication Data

US 2008/0033351 A1    Feb. 7, 2008

Related U.S. Application Data

(60) Provisional application No. 60/835,488, filed on Aug. 4, 2006.

(51) Int. Cl.
*A61F 2/16*  (2006.01)
*A61F 9/00*  (2006.01)
*A61K 9/00*  (2006.01)

(52) U.S. Cl.
CPC .............. *A61F 9/0017* (2013.01); *A61K 9/0051* (2013.01)

(58) Field of Classification Search
CPC ....... A61F 2/1662; A61F 2/167; A61F 2/143; A61F 2/146; A61F 2/147; A61F 2/1691; A61F 9/0017; A61F 9/007; A61F 9/00736; A61F 9/0008; G02B 1/041; A61M 37/0069; A61M 5/178; A61M 2005/3106; A61M 31/00; A61K 9/0051
USPC .............. 606/107, 108, 192; 604/58–60, 264, 604/236, 232, 244, 8, 205, 208, 521, 533, 604/167.01–167.04, 62, 57, 61, 63, 64, 130, 604/294, 295; 623/4, 4.1, 6.12
See application file for complete search history.

(56) References Cited

U.S. PATENT DOCUMENTS

| 2,513,014 | A | 6/1950 | Fields |
| 2,717,599 | A | 9/1955 | Huber |

(Continued)

FOREIGN PATENT DOCUMENTS

| EP | 0197718 | 10/1986 |
| EP | 0270257 | 6/1988 |

(Continued)

OTHER PUBLICATIONS

Aukunuru et al., "In Vitro Delivery of Nano- and Micro-Particles to Human Retinal Pigment Epthelial (ARPE-19) Cells", Drug Delivery Technology, vol. 2, No. 2, Mar./Apr. 2002, pp. 50-57.

(Continued)

*Primary Examiner* — Jocelin Tanner
(74) *Attorney, Agent, or Firm* — Laura L. Wine; Joel B. German; Debra D. Condino

(57) ABSTRACT

Ocular implant delivery assemblies are provided which include a cannula having a lumen extending therethrough, a proximal end, a proximal end opening, a distal end, a distal end opening, and a lumen extending through the cannula. A cap is provided having a closed distal end, being in contact with the outer wall of the cannula, and covering the distal end and the distal end opening of the cannula, the cap being structured to allow the distal end and the distal end opening of the cannula to pass through the cap as the cannula is passed into an eye. An ocular implant is located in the lumen. The implant may be sealed in the cannula without the addition of a liquid carrier or it may be contained in a liquid carrier medium in the cannula. The implant may be made up of a number of microparticles having different compositions or different forms. The assembly also includes a sleeve located on the proximal end of the cannula and suitable for coupling the assembly to a syringe containing a pushing gel.

20 Claims, 5 Drawing Sheets

(56) References Cited

U.S. PATENT DOCUMENTS

| | | |
|---|---|---|
| 3,220,413 A | 11/1965 | Sunnen |
| 3,238,941 A | 3/1966 | Klein et al. |
| 3,698,390 A | 10/1972 | Ferris |
| 3,937,370 A | 2/1976 | Witty |
| 3,941,128 A | 3/1976 | Baldwin |
| 4,105,030 A | 8/1978 | Kercso |
| 4,144,317 A | 3/1979 | Higuchi et al. |
| 4,304,765 A | 12/1981 | Shell et al. |
| 4,383,992 A | 5/1983 | Lipari |
| 4,521,210 A | 6/1985 | Wong |
| 4,597,753 A | 7/1986 | Turley |
| 4,668,506 A | 5/1987 | Bawa |
| 4,727,064 A | 2/1988 | Pitha |
| 4,799,478 A | 1/1989 | Fedorov et al. |
| 4,803,075 A | 2/1989 | Wallace et al. |
| 4,846,809 A * | 7/1989 | Sims ............................ 604/198 |
| 4,850,970 A | 7/1989 | Sutherland |
| 4,853,224 A | 8/1989 | Wong |
| 4,900,304 A * | 2/1990 | Fujioka et al. .................. 604/60 |
| 4,907,587 A | 3/1990 | Fedorov et al. |
| 4,915,686 A | 4/1990 | Frederick |
| 4,920,104 A | 4/1990 | DeVore et al. |
| 4,941,874 A | 7/1990 | Sandow et al. |
| 4,959,217 A | 9/1990 | Sanders |
| 4,997,652 A | 3/1991 | Wong |
| 5,014,717 A | 5/1991 | Lohrmann |
| 5,059,172 A | 10/1991 | Sutherland et al. |
| 5,098,443 A | 3/1992 | Parel et al. |
| 5,164,188 A | 11/1992 | Wong |
| 5,188,607 A * | 2/1993 | Wu ........................... 604/167.03 |
| 5,219,339 A | 6/1993 | Saito |
| 5,250,026 A | 10/1993 | Ehrlich et al. |
| 5,256,408 A | 10/1993 | Babcock et al. |
| 5,279,554 A | 1/1994 | Turley |
| 5,284,479 A | 2/1994 | DeJong |
| 5,324,718 A | 6/1994 | Loftsson |
| 5,332,582 A | 7/1994 | Babcock et al. |
| 5,336,206 A | 8/1994 | Shichman |
| 5,378,475 A | 1/1995 | Smith et al. |
| 5,443,505 A * | 8/1995 | Wong et al. ..................... 623/4.1 |
| 5,451,213 A | 9/1995 | Teicher et al. |
| 5,466,233 A | 11/1995 | Weiner et al. |
| 5,476,511 A | 12/1995 | Gwon et al. |
| 5,494,901 A | 2/1996 | Javitt et al. |
| 5,501,856 A | 3/1996 | Ohtori et al. |
| 5,516,522 A | 5/1996 | Peyman et al. |
| 5,576,311 A | 11/1996 | Guy |
| 5,582,591 A * | 12/1996 | Cheikh ........................... 604/500 |
| 5,616,123 A | 4/1997 | Cheikh |
| 5,651,774 A * | 7/1997 | Taranto et al. ................ 604/198 |
| 5,656,026 A * | 8/1997 | Joseph ............................. 604/9 |
| 5,695,463 A * | 12/1997 | Cherif-Cheikh ............... 604/60 |
| 5,725,521 A | 3/1998 | Mueller |
| 5,746,718 A * | 5/1998 | Steyn ............................ 604/192 |
| 5,766,242 A | 6/1998 | Wong et al. |
| 5,770,589 A | 6/1998 | Billson et al. |
| 5,807,400 A | 9/1998 | Chambers et al. |
| 5,817,075 A * | 10/1998 | Giungo ........................... 604/294 |
| 5,824,001 A | 10/1998 | Erskine |
| 5,824,072 A | 10/1998 | Wong |
| 5,869,079 A | 2/1999 | Wong et al. |
| 5,876,373 A | 3/1999 | Giba et al. |
| 5,908,404 A * | 6/1999 | Elliott ........................... 604/506 |
| 5,941,250 A | 8/1999 | Aramant et al. |
| 5,957,892 A | 9/1999 | Thorne |
| 6,074,661 A | 6/2000 | Olejnik et al. |
| 6,107,347 A | 8/2000 | Francese et al. |
| 6,117,443 A | 9/2000 | Cherif-Cheikh |
| 6,120,786 A | 9/2000 | Cherif Cheikh |
| 6,142,972 A | 11/2000 | Cheikh |
| 6,159,218 A | 12/2000 | Aramant et al. |
| 6,190,350 B1 | 2/2001 | Davis et al. |
| 6,217,895 B1 | 4/2001 | Guo et al. |
| 6,251,418 B1 | 6/2001 | Ahern et al. |
| 6,271,216 B1 | 8/2001 | Mello et al. |
| 6,331,313 B1 | 12/2001 | Wong et al. |
| 6,395,294 B1 | 5/2002 | Peyman |
| 6,407,079 B1 | 6/2002 | Muller et al. |
| 6,450,937 B1 | 9/2002 | Mercereau et al. |
| 6,497,686 B1 * | 12/2002 | Adams et al. .................. 604/268 |
| 6,548,078 B2 | 4/2003 | Guo et al. |
| 6,554,760 B2 * | 4/2003 | Lamoureux et al. ............... 600/7 |
| 6,639,116 B2 | 10/2003 | Lever et al. |
| 6,648,857 B1 * | 11/2003 | Pedigo ........................... 604/192 |
| 6,699,493 B2 | 3/2004 | Wong |
| 6,713,081 B2 | 3/2004 | Robinson et al. |
| 6,719,750 B2 | 4/2004 | Varner et al. |
| 6,723,353 B2 | 4/2004 | Beck et al. |
| 6,899,717 B2 | 5/2005 | Weber et al. |
| 7,189,245 B2 | 3/2007 | Kaplan |
| 7,651,505 B2 | 1/2010 | Lubock et al. |
| 2002/0026176 A1 | 2/2002 | Varner et al. |
| 2002/0035264 A1 * | 3/2002 | Kararli et al. .................. 546/300 |
| 2002/0082609 A1 | 6/2002 | Green |
| 2002/0198174 A1 | 12/2002 | Lyons |
| 2003/0060763 A1 | 3/2003 | Penfold et al. |
| 2003/0171320 A1 | 9/2003 | Guyer |
| 2003/0208218 A1 * | 11/2003 | Kadziauskas et al. ......... 606/169 |
| 2004/0054374 A1 * | 3/2004 | Weber et al. ................... 606/107 |
| 2004/0057979 A1 * | 3/2004 | Wong et al. ..................... 424/428 |
| 2004/0077562 A1 | 4/2004 | Chandavarkar et al. |
| 2004/0152664 A1 | 8/2004 | Chang et al. |
| 2004/0170665 A1 | 9/2004 | Donovan |
| 2005/0032747 A1 * | 2/2005 | Bartolini et al. ................. 514/80 |
| 2005/0049605 A1 | 3/2005 | Vaquero et al. |
| 2005/0119737 A1 * | 6/2005 | Bene et al. ...................... 623/4.1 |
| 2005/0154399 A1 | 7/2005 | Weber et al. |
| 2006/0108012 A1 | 5/2006 | Barrow |
| 2006/0173060 A1 | 8/2006 | Chang et al. |
| 2007/0293873 A1 * | 12/2007 | Chang ........................... 606/107 |
| 2008/0097459 A1 | 4/2008 | Kammerlander |

FOREIGN PATENT DOCUMENTS

| | | |
|---|---|---|
| EP | 0 304 700 A | 3/1989 |
| EP | 0304700 | 3/1989 |
| EP | 0415504 | 3/1991 |
| EP | 0544948 | 9/1995 |
| EP | 1419748 | 11/2002 |
| EP | 1323450 | 7/2003 |
| WO | WO 91/12048 | 3/1991 |
| WO | WO 91/12048 A | 8/1991 |
| WO | WO 99/33512 | 7/1999 |
| WO | WO 99/53991 | 10/1999 |
| WO | WO 00/02564 | 1/2000 |
| WO | WO 02/089815 | 11/2002 |
| WO | WO 2004/026106 | 4/2004 |
| WO | WO 2004/069280 | 8/2004 |
| WO | WO 2004/087043 | 10/2004 |
| WO | WO 2005/055873 | 6/2005 |
| WO | WO 2006/071554 | 7/2006 |
| WO | WO 2006/071554 A | 7/2006 |

OTHER PUBLICATIONS

Beer et al., "Intraocular Concentration and Pharmacokinetics of Triamcinolone Acetonide After a Single Intravitreal Injection", Ophthalmology, vol. 110, No. 4, Apr. 2003, pp. 681-686.

Cheng et al., "Intravitreal Sustained-Release Dexamethasone Device in the Treatment of Experimental Uveitis", Investigatative Ophthalmology & Visual Science, Feb. 1995, vol. 36, No. 2, pp. 442-453.

Crabb et al., "Cloning of the cDNAs encoding the cellular retinaldehyde-binding protein from bovine and human retina and comparison of the protein structures", J. Biol. Chem., 265(35), 1988, pp. 18688-18692.

Dunn et al., ARPE-19, a human retinal pigment epithelial cell line with differentiated properties, Exp. Eye Res 62 (1996), pp. 155-169.

Enyedi et al., "An Intravitreal Device Providing Sustained Release of Cyclosporine and Dexamethasone", Current Eye Research (1995) pp. 549-557.

(56) References Cited

OTHER PUBLICATIONS

Klimanskaya et al., "Derivation and comparative assessment of retinal pigment epithelium from human embryonic stem cells using transcriptomics", Cloning and Stem Cells 6(3), 2004, 99. 217-245.

Kochinke et al., "Biodegradable Drug Delivery System for Uveitis Treatment", Investigative Ophthalmology & Visual Science, Feb. 15, 1996, vol. 37, No. 3, 186-B98.

Rao et al., "Preparation and Evaluation of Ocular Inserts Containing Norfloxacin", Turk. J. Med. Sci. (2004) 34, pp. 239-246.

Rogojina et al., "Comparing the use of affymetrix to spotted oligonucleotide microarrays using two retinal pigment epithelium cell lines", Molecular Vision, 9, 2003, pp. 482-496.

Streilein et al., "Ocular Immune Privilege: Therapeutic Opportunities from an Experiment of Nature", Nature Review Immunology (2003), 3, pp. 879-889.

USP 23; NF 18 (1995) pp. 1790-1798.

Yeung et al., "Cytotoxicity of Triamcinolone on Cultured Human Retinal Pigment Epithelial Cells: Comparison with Dexamethasone and Hydrocortisone", Jpn. J. Ophthal., 48 (2004), pp. 236-242.

\* cited by examiner

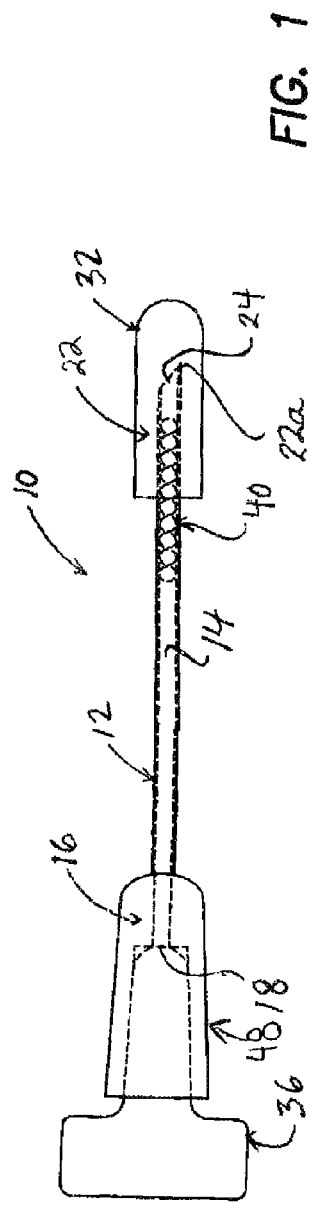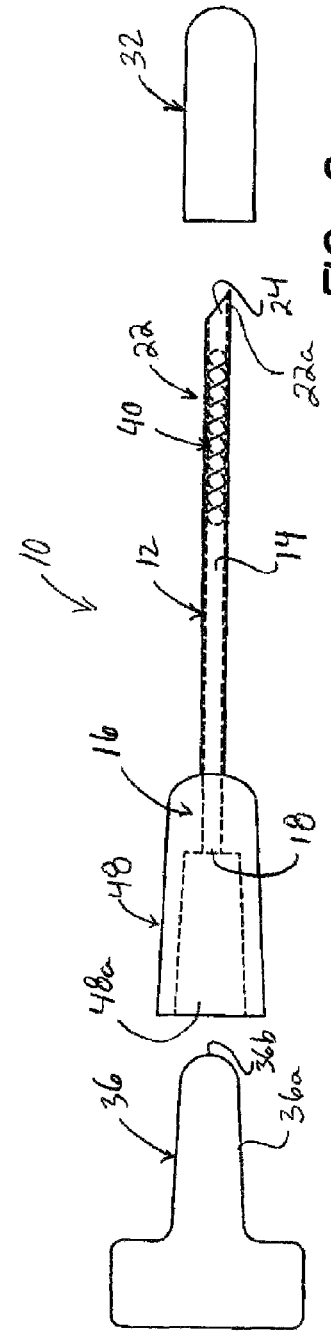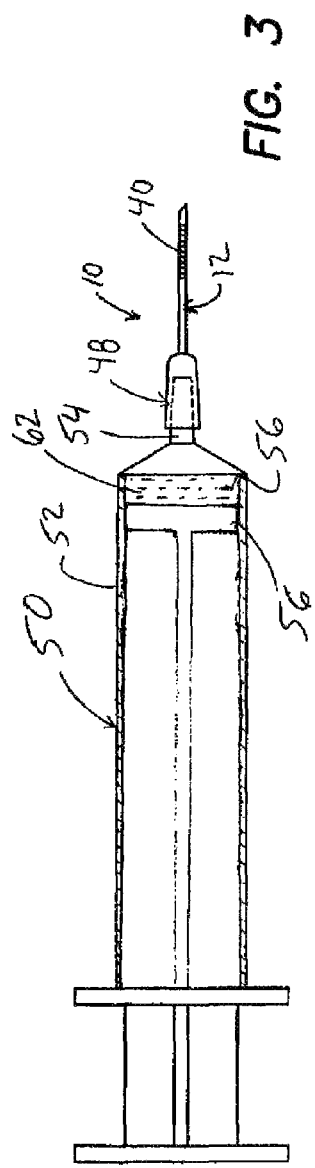

OCULAR IMPLANT DELIVERY ASSEMBLIES WITH DISTAL CAPS

RELATED APPLICATION

This application claims the benefit of Application Ser. No. 60/835,488, filed Aug. 4, 2006, the disclosure of which is incorporated in its entirety herein by reference.

BACKGROUND

The present invention generally relates to apparatus useful in implanting ocular implants in eyes. More particularly, the invention relates to pre-loaded ocular implant delivery assemblies for delivering, placing, positioning and the like, ocular implants in an eye, for example, at one or more of various locations in an eye, for example, a mammalian eye.

The mammalian eye is a complex organ comprising an outer covering including the sclera (the tough white portion of the exterior of the eye) and the cornea (the clear outer portion covering the pupil and iris). In a medial cross section, from anterior to posterior, the eye comprises features including, without limitation: the cornea, the anterior chamber (a hollow feature filled with a watery, clear fluid called the aqueous humor and bounded by the cornea in the front and the lens in the posterior direction), the iris (a curtain-like feature that can open and close in response to ambient light), the lens, the posterior chamber (filled with a viscous fluid called the vitreous humor), the retina (the innermost coating of the back of the eye and comprising light-sensitive neurons), the choroid (an intermediate layer providing blood vessels to the cells of the eye), and the sclera. The posterior chamber comprises approximately $2/3$ of the inner volume of the eye, while the anterior chamber and its associated features (lens, iris etc.) comprise about $1/3$ of the eye's inner volume.

Ocular implants containing one or more therapeutic components combined with matrix components, such as polymeric components, have been proposed for use, for example, to treat conditions/diseases of the eye. Such implants have been suggested for use at various locations in the eye, for example, in the vitreous, subconjunctivally, anterior chamber and posterior chamber of the eye.

Although such prior art implants have taken on various shapes, forms and configurations, one very useful implant form is a plurality of variously sized microparticles. For example, intravitreal injection of conventional microparticles, which average about 1-100 microns in size, is known and has been previously practiced. This injection of such microparticles is usually conducted using the microparticles suspended in a liquid aqueous medium.

Another type of implant that has been found to be very useful is in the form of a rod shape. Dry delivery in the eye of extruded, rod shaped implants, for example having diameters of about 450 microns and maximum lengths of 3-6 millimeters, has been successfully accomplished. However, it would be highly desirable to reduce the diameter of the implant in order to allow the use of a narrower gauge needle for injection. Reducing the diameter of such rod shaped implants often reduces the strength of the implant so that it breaks up during handling. Moreover, as such a rod shaped implant is reduced in diameter, the length of the implant gets much longer (so as to deliver an equal amount of therapeutic component to the eye) making the implant impractical for use.

It would be beneficial to provide assemblies including ocular implants that are useful in delivering ocular implants to eyes which are pre-packaged and allow for safe, long-term storage of the ocular implant. It would also be beneficial to provide assemblies containing ocular implants effective in conveniently treating an eye in a single procedure and using a delivery needle that is as narrow as possible.

SUMMARY

New ocular implant delivery assemblies have been discovered. The present assemblies are useful in conveniently and controllably placing ocular implants, for example, substantially biodegradeable drug delivery ocular implants containing pharmaceutical compositions, into an eye in a single, relatively straightforward procedure without causing any substantial breakage or other damage to the implant. Further, the apparatus enables injection of such implants, for example but not limited to such implants in the form of one or more thin filaments or microparticles, into an eye by means of an exceptionally small cannula or needle, thereby reducing invasiveness of the injection procedure and accelerating healing relative to injection of implants by means of more conventionally sized needles.

DEFINITIONS

For the purposes of this description, the words or terms set forth herein have the following definitions, unless the context of the word indicates a different meaning.

As used herein, an "ocular implant" or "intraocular implant" refers to a device, element, or elements, that is structured, sized, or otherwise configured to be placed "in an eye", including the subconjunctival space. Ocular or intraocular implants are generally biocompatible with physiological conditions of an eye and do not cause adverse side effects. Ocular or intraocular implants may be placed in an eye without disrupting vision of the eye.

As used herein, "implant" refers to an ocular or intraocular implant or a drug delivery device which can be inserted into any number of locations in the eye, and which is designed such that a controlled amount of desired drug or therapeutic can be released over time. Such implants, which can be solid or semi-solid, are biocompatible, and in many but not all cases are formed of a bioerodible substance, such as a bioerodible polymer. "Microimplants" refers to such implants having a sufficiently small cross-sectional area that they can be delivered by assemblies according to the invention that result in self-sealing of the eye at the puncture site associated with the delivery. In particular, such microimplants have dimensions such that they are deliverable through 21 gauge or 22 gauge or preferably smaller gauge cannulas. Thin wall versions of 21 gauge needles can be manufactured having inner or lumen diameters of up to 0.028 inches (711 microns), thus cylindrical microimplants deliverable through such sized cannulas will have outer diameters of less than 0.028 inches (711 microns). Thin wall versions of 22 gauge needles can have inner diameters of up to 0.023 inches (585 microns), and thus cylindrical microimplants with diameters of less than 0.023 inches (585 microns) will be deliverable through such sized cannulas. Thin wall versions of 25 gauge cannulas or needles allow implants having diameters of about 0.015 inch (about 381 microns) or less, for example, in a range of about 0.014 inch (about 355 microns) to about 0.015 inch (about 380 microns) to be delivered through such cannulas. Microimplants can also have non-circular cross-sectional geometries for delivery through cannulas having corresponding cross-sectional geometries. Where the micro-implant has non-circular cross-section, the cross-sectional area may be up to 0.00025 square inches (0.16 square millimeters) or more, depending on the particular cross-sectional geometry.

As used herein, "self sealing" methods of delivering microimplants into the eye refers to methods of introducing microimplants through a cannula and into desired locations of a patient's eye without the need for a suture, or other like closure means, at the cannula puncture site. Such "self sealing" methods do not require that the puncture site completely seal immediately upon withdrawal of the cannula, but rather that any initial leakage is minimum and dissipates in short order such that a surgeon or another equally skilled in the art, in his or her good clinical judgment, would not be compelled to suture or otherwise provide other like closure means to the puncture site.

As used herein, a "therapeutic component" refers to a portion of an ocular or intraocular implant comprising one or more therapeutic agents or substances used to treat a medical condition of the eye. The therapeutic component may be a discrete region of an ocular or intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, a "pharmaceutical composition" is a formulation which contains at least one active ingredient (for example a corticosteroid) as well as, for example, one or more excipients, buffers, carriers, stabilizers, preservatives and/or bulking agents, and is suitable for administration to a patient to achieve a desired effect or result. The pharmaceutical compositions disclosed herein can have diagnostic, therapeutic, cosmetic and/or research utility in various species, such as for example in human patients or subjects.

As used herein, a "drug release sustaining component" refers to a portion of the ocular or intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding.

As used herein, "liquid carrier medium" or liquid medium" means material that is substantially flowable when at room temperature (i.e. about 20 to about 25 degrees Celsius), and includes gels and other viscous flowable materials that are useful to facilitate delivery of solid or semi-solid implants through a cannula of the inventive assemblies.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An "anterior ocular condition" is a disease, ailment or condition which affects or which involves an anterior (i.e. front of the eye) ocular region or site, such as a periocular structure, for example, a periocular muscle, an extraocular structure, an orbital structure, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A "posterior ocular condition" is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time is required to achieve release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

In a broad aspect of the invention, ocular implant delivery assemblies are provided, the assemblies generally comprising a cannula having a proximal end, a proximal end opening, a distal end, a distal end opening, and a lumen extending through the cannula. The assemblies further comprise a removable distal closure element positioned relative to the cannula to close the distal end, and a removable proximal closure element positioned relative to the cannula to close the proximal end. Advantageously, the assemblies further include an ocular implant located in the cannula and sized and adapted for implantation in an eye. The assemblies are designed to be coupled to a syringe, for example, a gel containing syringe, or other device, for example and without limitation, a push-rod device and the like, effective to deliver the implant from the cannula and into a target region of an eye.

In another aspect of the present invention, ocular implant delivery assemblies are provided which generally comprise a cannula having a proximal end, a proximal end opening, a distal end, a distal end opening, and a lumen extending through the cannula; an ocular implant sized and structured for implantation in an eye located in the lumen of the cannula; and a distal plug, for example and without limitation, a bioerodible polymeric distal plug, that is a distal plug comprising a bioerodible polymeric material, positioned relative to the cannula to reduce the size of or close the distal end opening of the cannula. In one embodiment, the distal plug is located in or substantially directly adjacent the lumen of the cannula. The distal plug may be located distal of the ocular implant in the lumen and/or at or near the distal end of the cannula. The distal plug is structured, when in place relative to the cannula, to prevent the ocular implant from passing out of the distal end opening of the cannula. In addition, the distal plug may be effective in closing, for example and without limitation, in sealing, the distal end opening of the cannula. The lumen can be the lumen of a 25 gauge or higher gauge syringe needle. The plug can comprise, for example and without limitation, a hydroxypropyl methyl cellulose (HPMC). The plug is removable or can be pierced so as to permit passage of the implant out through the distal opening of the cannula by applying a distally extending force, for example and without limitation, by advancing a plunger, in the lumen of the cannula.

In one embodiment, a proximal plug, for example and without limitation, a bioerodible polymeric proximal plug, that is a distal plug comprising a bioerodible polymeric material, is positioned relative to the cannula to reduce the size of or close the proximal end opening of the cannula. In one embodiment, the proximal plug is located in or substantially directly adjacent the lumen of the cannula. The proximal plug may be located proximal of the ocular implant in the lumen and/or at or near the proximal end of the cannula. The proximal plug is structured, when in place relative to the cannula, to prevent the ocular implant from passing out of the proximal end opening of the cannula. In addition, the proximal plug may be effective in closing, for example and without limitation, in sealing the proximal end opening of the cannula.

When it is desired to pass the ocular implant into an eye through the distal end opening of the cannula, the distal plug and/or the proximal plug may be removed prior to coupling the cannula to a force applying device, e.g., syringe, push-rod device and the like, to urge the ocular implant into an eye. Alternately, the distal plug and/or proximal plug may be maintained in place as the cannula is coupled to a force applying device. In this embodiment, when the force applying device is activated, for example and without limitation, manually activated, the proximal plug and/or the distal plug are urged distally by the force generated. Thus, the distal plug and/or the proximal plug pass into the eye along with the ocular implant. In this embodiment, it is advantageous that the distal plug and/or proximal plug be compatible with the region of the eye in which the ocular implant is placed. In one embodiment, the distal plug and/or proximal plug are soluble in the environment of the eye region in which the ocular implant is placed.

In another broad aspect of the invention, ocular implant delivery assemblies are provided which generally comprise a cannula having an outer wall, a proximal end, a proximal end opening, a distal end, a distal end opening, and a lumen extending through the cannula; an ocular implant sized and structured for implantation in an eye located in the lumen of the cannula; and a cap having a closed distal end. The cap is in contact with the outer wall of the cannula, and covers the distal end and distal end opening of the cannula. The cap is structured to allow the distal end and distal end opening of the cannula to pass through the cap, for example and without limitation, to pierce and pass through the cap, as the cannula is passed into an eye. The embodiments of the present assemblies which include a cap, may also include a removable proximal closure element positioned relative to the cannula to close the proximal end opening of the cannula.

Assemblies which include any of a removable distal closure element, distal plug and cap, as described herein, may include either or both of a removable proximal closure element and a proximal plug. Moreover, any of a distal closure element, distal plug, cap, proximal closure element or proximal plug may be used alone. Assemblies which include any one of such elements and any two or more of such elements are included within the scope of the present invention.

The present assemblies may include, for example, may be coupled to, a syringe, for example, a gel containing syringe, or other device, for example and without limitation, a push-rod device. effective to at least assist in delivering the implant from the cannula into an eye, for example, into a target region of an eye.

In one aspect of the invention, the assemblies are structured to preserve structural and/or chemical integrity of the implant during an extended period of time, for example, during a period of time extending from when the assembly is produced or manufactured to when the assembly is used to deliver the ocular implant into an eye.

For example, the assembly may be structured to prevent light, moisture and air from entering the cannula prior to use of the assembly. For example, the cannula may be substantially opaque to light to substantially prevent degradation, more specifically, photodegradation, of the implant. Further, the proximal closure element and the proximal plug, and the distal closure element, the distal plug and the cap, may be effective to seal the cannula so as to prevent air and/or moisture from entering the cannula.

In some embodiments, the cannula comprises a rigid, preferably metallic, needle preferably having a substantially circular cross section. The distal end is sharpened or otherwise suitable for being introduced into an eye.

In one embodiment, the cannula has sufficient sharpness to be passed into an eye. In embodiments in which a cap is provided covering the distal end and distal end opening of the cannula. The cap is structured, for example, has sufficient softness, to be pierced by the cannula in passing the cannula into an eye, advantageously without substantially detrimentally affecting the cannula or the eye into which the cannula is passed. For example, the cap may be structured to allow the distal end and distal end opening to pierce and pass through the cap without substantially detrimentally affecting the sharpness of the distal end of the cannula. Thus, the cap can remain on the cannula and cover the distal end and distal end opening of the cannula until the cannula is passed into an eye. This feature of the present invention facilitates maintaining the ocular implant in the cannula until it is to be delivered into an eye. In other words, the cap prevents the ocular implant from leaving the lumen of the cannula until it is desired that the implant pass from the lumen into the eye. This is highly advantageous in that the risk of losing the implant or portion of the implant from the cannula prior to delivery into an eye is reduced or even substantially eliminated.

Advantageously, the cap may be structured, for example, have sufficient softness, to move proximally along the cannula as the cannula is passed into an eye. This is a very useful feature of the present invention. For example, the position of the cap, for example, the pierced cap, on the cannula as the distal portion of the cannula is passed into an eye provides a direct visual indication of the extent to which the cannula is in the eye. In other words, the operator, for example and without limitation, the physician, surgeon and the like, placing the implant into the eye is provided a direct visual indication, for example, by observing the distance between the cap and the proximal end region of the cannula, of the length of the cannula that has been passed into the eye. Although passing the cannula into an eye is often done using x-ray and/or other imaging methodologies, the direct visual indication of how much of the cannula has been passed into an eye provided by the present invention is an at least added control and/or safety feature for use by the operator, and provides for added control/safety of the procedure for implanting ocular implants.

The cannula may be configured to contain and deliver an ocular implant having very small dimensions, for example, a microimplant. For example, the cannula may have an outer diameter of 0.032 inches (813 microns) or less. In further embodiments, the cannula is configured to have an outer diameter of 0.028 inches (711 microns) or less or 0.025 inches (635 microns) or less. Alternatively, the cannula has a non-circular transverse cross-section. In these embodiments, the cannula can have a transverse cross-sectional area of up to about 0.0008 square inches (0.52 square millimeters) or greater, depending on the particular cannula geometry. Cannulas having such configurations are able to receive and deliver very small ocular implants, i.e., so-called "microimplants" and effectively allow for self-sealing of the delivery site.

The assemblies are suitable to deliver ocular implants to a target location of the eye where the implant will be most therapeutically effective. Various sites exist in the eye for implantation of a drug delivery device or implant, such as the vitreous of the eye, anterior or posterior chambers of the eye, or other areas of the eye including intraretinal, subretinal, intrachoroidal, suprachoroidal, intrascleral, episcleral, subconjunctival, intracorneal or epicorneal spaces or sub-tenon's space.

Advantageously, in some embodiments of the invention, the cannula has an outside diameter no larger than a 22 gauge syringe needle. For example, the cannula may have an outside diameter no larger than a 25 gauge syringe needle, or about equal to the outside diameter of a 27 gauge syringe needle or about equal to the outside diameter of a 30 gauge syringe needle.

In some embodiments the lumen has a diameter of less than about 350 microns, or less than about 300 microns, or even less than about 250 microns. In a specific embodiment, the cannula is a 25 gauge needle having a lumen with a diameter of 262 microns or 312 microns. In another specific embodiment, the cannula is a 27 gauge needle having a lumen with a diameter of 210 microns or 287 microns.

In some embodiments, substantially no liquid material is present in the lumen with the ocular implant. As will be explained in greater detail hereinafter, in these embodiments, the implant is stored in the cannula in a substantially dry state, more specifically, without the inclusion of a liquid carrier. Dry storage of the implant in some instances is effective to prolong the shelf life of the drug or drugs, particularly drugs which are soluble or partially soluble in aqueous based carriers.

In other embodiments, the assembly further comprises a carrier medium comprising, for example, an aqueous component and a viscosity inducing component, the liquid carrier medium being located in the cannula with the ocular implant. In these embodiments, the ocular implant may be of a make-up such that the implant is insoluble in the carrier medium, for example, when stored in the cannula at room temperature, but is soluble when placed in the environment of the eye, for example, the vitreous of the eye. In some embodiments, the ocular implant comprises a plurality of particles suspended in a suitable carrier medium.

The distal closure element covers the distal end and the distal end opening of the cannula. The distal closure element preferably comprises a polymeric material, for example, a silicone polymeric material. The distal closure element may be self secured to the cannula, for example, by being press fit to the cannula. In some embodiments, the distal closure element is adhesively secured to the cannula. Preferably, the distal closure element is manually removable from the cannula.

The distal plug and the proximal plug, when employed, may be fitted and/or otherwise placed into the distal opening and proximal opening, respectively, of the cannula. In one embodiment, the distal plug and proximal plug are provided in a liquid or flowable form, for example and without limitation, as a liquid, a liquid solution, a liquid-containing suspension, a liquid-containing emulsion and the like. This liquid or flowable form is coated onto the distal end or proximal end of the cannula, and is allowed to pass into the lumen of the cannula through the distal end opening or the proximal end opening, respectively, to a limited extent. The cannula is then subjected to conditions effective to cause a solid distal plug or a solid proximal plug to form. Such plug or plugs remain in place relative to the cannula until the ocular implant in the cannula is to be placed into an eye, as described elsewhere herein.

With regard to the embodiments in which a cap is employed, the cap is preferably self-secured to the cannula, for example, by being friction fitted to the cannula. Advantageously, the cap is not adhesively secured to the cannula. Although the cap may be manually removable from the cannula, it is preferred that the cap remain on the cannula as the cannula is passed into an eye. Thus, the securement between the cap and the cannula advantageously is such that the cap moves proximally along the cannula as the distal portion of the cannula is passed into an eye. In other words, the cap is advantageously secured to the cannula sufficiently strongly to reduce or substantially eliminate the risk of an unintended removal of the implant from the cannula prior to placing the implant in an eye while, at the same time, being such as to allow the cap to move proximally on the cannula as the distal portion of the cannula is passed into an eye.

Advantageously, the distal end of the cannula is structured to facilitate entry of a distal portion of the cannula into an eye. For example, the distal end of the cannula may be beveled or sharpened.

The proximal closure element is positioned in or directly adjacent the proximal end opening of the cannula and is preferably structured to sealingly close the proximal end opening of the cannula. In some embodiments, the proximal closure element comprises a polymeric material, for example, a silicone polymeric material. Preferably, the proximal closure element is structured to be manually removable from the cannula.

In some embodiments, the assembly further comprises a sleeve, for example, an enlarged sleeve, coupled to the cannula and extending proximally thereof. The sleeve is structured and positioned to facilitate coupling of the cannula to a syringe or other activating device. The proximal closure element may be structured to be coupled to, for example, received by, the sleeve. Furthermore, the sleeve may be structured to facilitate the sealing of the proximal end opening with the proximal closure element.

Generally, the plurality of particles located in the lumen includes a number of particles in a range of about 5 or about 10 or about 25 to about 75 or about 100 or about 150 or about 200 particles.

In some embodiments, the implant comprises a plurality of particles having the same or different compositions, for example, in the same or different proportions relative to one another. In another aspect of the invention, the implant comprises a plurality of particles comprising different compositions. The compositions may include at least one therapeutic component effective to provide a therapeutic effect when released into an eye, and at least one of a biodegradable component, a non-biodegradable component, and combinations thereof. For example, the plurality of particles comprises a biodegradable polymer in combination with the at least one therapeutic component. In some situations, the implant comprises a plurality of different particles having the same or different release rates and/or delayed release rates.

Further, the plurality of particles making up the ocular implant may be in one or more different forms, for example, different shapes and/or sizes. For example, the particles may be in the form of particles selected from the group consisting of spheres, rods, filaments, plaques and the like and combinations thereof.

In a more specific embodiment of the invention, the particles making up the implant comprise microspheres, for example, a plurality of microspheres, for example, a plurality of substantially uniformly sized microspheres. For example, the plurality of substantially uniformly sized microspheres includes a smallest particle and a largest particle. The largest particle has a maximum diameter within about 20%, preferably about 10%, more preferably about 5%, of the maximum diameter of the smallest particle. In other embodiments, the implant comprises a plurality of microspheres having different sizes.

In one aspect of the invention, the implant comprises a plurality of particles including at least one particle having a first form and at least one particle having a second form that is different from the first form. In some embodiments, the implant comprises at least one rod-shaped particle and at least one microsphere. As a more specific example, the implant may comprise a plurality of rods comprising a first therapeutic component, and a plurality of microspheres comprising a second therapeutic component that is different than the first therapeutic component.

In a broad aspect of the invention, the ocular implant comprises a therapeutic component and a polymer component. For example, the implant may comprise particles of active, therapeutic agents contained in a bioerodible polymer. In some embodiments, the implant comprises a first particle including a therapeutic component and a polymer component having a first release rate, and the at least one different particle including the same or a different therapeutic component and a polymer component having a second release rate that is different than the first release rate.

Many combinations and/or forms of particles making up a single ocular implant useful in the present assemblies are possible, and are considered to be included within the scope of the present invention.

Preferably, the maximum transverse dimension, for example diameter, of each particle of the plurality of particles is at least about 70% of the diameter of the lumen, for example, is at least about 80% of the diameter of the lumen, for example, is at least about 90% of the diameter of the lumen.

The present assemblies are structured to be coupled or attached to an injector mechanism, for example, a hand-held syringe or a push-rod device or similar instrument or device. For example, the assemblies are structured to be coupleable to a conventional or standard medical syringe including a barrel for containing a fluid, a hub on a distal end of the barrel and capable of being connected to the sleeve of the present assemblies, and a plunger or other actuating element. In a more specific embodiment, the syringe is a 0.5 to 1.0 ml syringe. The syringe is suitable for containing a fluid, more specifically a liquid medium, which is used to carry the implant located in the assemblies of the invention into an eye upon injection from the distal end of the cannula, for example, upon actuation of the plunger. The liquid medium may be, for example, a substantially inert or substantially inactive material, or, alternatively, the liquid medium may comprise an active component, for example, a therapeutic component, intended to be introduced into an eye along with the ocular implant.

In other embodiments, the cannula may be coupled to a push-rod device, for example, such as disclosed in Weber et al U.S. Pat. No. 6,899,717. Briefly, such push-rod devices include a longitudinally extending rod which is positioned relative to the cannula so that the distal end of the rod is in contact with the implant in the lumen of the cannula. Upon the application of a force, for example, a manual force, to the rod, the rod moves distally. Such distal movement of the rod, urges or pushes the implant out of the distal end opening of the cannula and into an eye.

Advantageously, the present assemblies can be practiced or provided to treat an anterior ocular condition and/or a posterior ocular condition. For example, in an especially advantageous embodiment, the assemblies can be practiced or provided to treat a condition of the posterior segment of a mammalian eye, such as a condition selected from the group consisting of macular edema, dry and wet macular degeneration, choroidal neovascularization, diabetic retinopathy, acute macular neuroretinopathy, central serous chorioretinopathy, cystoid macular edema, and diabetic macular edema, uveitis, retinitis, choroiditis, acute multifocal placoid pigment epitheliopathy, Behcet's disease, birdshot retinochoroidopathy, syphilis, lyme, tuberculosis, toxoplasmosis, intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; retinal arterial occlusive disease, anterior uveitis, retinal vein occlusion, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy, angioid streaks, familial exudative vitreoretinopathy, and Eales disease; traumatic/surgical conditions such as sympathetic ophthalmia, uveitic retinal disease, retinal detachment, trauma, photocoagulation, hypoperfusion during surgery, radiation retinopathy, and bone marrow transplant retinopathy; proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; punctate inner choroidopathy, acute posterior multifocal placoid pigment epitheliopathy, myopic retinal degeneration, acute retinal pigment epithelitis, retinitis pigmentosa, proliferative vitreal retinopathy (PVR), age-related macular degeneration (ARMD), diabetic retinopathy, diabetic macular edema, retinal detachment, retinal tear, uveitis, cytomegalovirus retinitis and glaucoma and conditions involving ocular degeneration, such as neurodegeneration of retinal ganglion cells.

Incorporated herein by this specific reference is the entire disclosure of each of the following documents: U.S. Patent Application for APPARATUS AND METHODS FOR IMPLANTING PARTICULATE OCULAR IMPLANTS, having Ser. No. 11/455,392, filed on Jun. 19, 2006, commonly assigned herewith; U.S. patent application Ser. No. 10/917,909, filed on Aug. 13, 2004; U.S. patent application Ser. No. 11/303,462, filed on Dec. 15, 2005; and U.S. patent application Ser. No. 11/091,977, filed on Mar. 28, 2005.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

DRAWINGS

The following Drawings illustrate some but not all of the aspects and advantages of the present invention.

FIG. 1 is a cross-sectional view of an assembly in accordance with the invention, the apparatus including a cannula for implanting an ocular implant in a region of a mammalian eye, a removable distal closure element, a removable proximal closure element, and an ocular implant located in the cannula.

FIG. 2 is a cross-sectional view of the assembly shown in FIG. 1 having both the removable distal closure element and the removable proximal closure element disengaged or removed from the cannula, prior to use of the assembly for injecting the implant into an eye.

FIG. 3 is a partially cross-sectional view of the assembly shown in FIG. 1 in which the cannula is coupled to a syringe containing a carrier fluid.

DESCRIPTION

Figure 4:
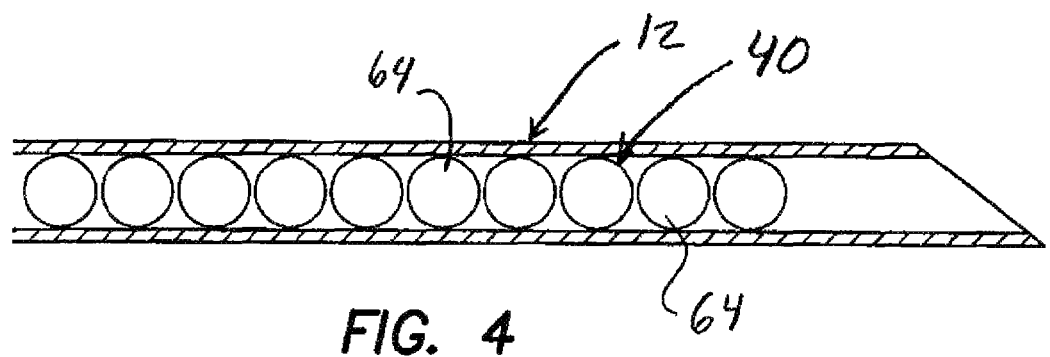
FIG. 4 is an enlarged cross-sectional view of a distal portion of the cannula shown in FIG. 1, showing the ocular implant comprising a plurality of substantially uniformly sized microspheres.

As described herein, assemblies for facilitating administration of therapeutic agents through the use of one or more ocular or intraocular implants are provided, and are useful for improving treatment of a variety of ocular conditions.

With reference to FIGS. 1 and 2, an assembly in accordance with the invention for implanting an ocular implant in an eye is shown generally at 10. The assembly 10 comprises a cannula 12 having a lumen 14 extending therethrough. The cannula 12 has a proximal end 16, a proximal end opening 18, a distal end 22, and a distal end opening 24. As shown, the assembly 10 further comprises a removable distal closure element 32 positioned relative to the cannula 12 to close, for example, to be sealingly coupled to, the distal end 22. The assembly further comprises a removable proximal closure element 36 positioned relative to the cannula 12 to close, for example, to be sealingly coupled to, the proximal end 16 of the cannula 12. In addition, the assembly 10 comprises an ocular implant 40 located in the cannula 12. The ocular implant 40 is sized and adapted for implantation in an eye.

The assembly 10 is structured to provide convenient, safe packaging of ocular implants prior to placement of such implants in an eye. In use, the assembly provides for sterile containment of an ocular implant in a manner such that the implant will not be subject to significant degradation or other significant chemical or structural changes when stored in the cannula over an extended period of time. By "extended period of time" is generally meant herein as a period of time of at least about 1 month, at least about 3 months, at least about 6 months, at least about one year, at least about two years, or even greater or longer.

For example, the cannula 12 may be made of made of metal, such as stainless steel, or other suitable material. In order to allow the cannula to easily pass into an eye, the cannula is preferably made of a generally rigid material. To prevent photo-initiated degradation of the implant, the cannula, and in one or more embodiments one or more other components of the assembly, are preferably made of materials that are substantially opaque to light, for example, light which can cause such degradation.

As shown, the cannula 12 includes a distal tip 22a structured to facilitate entry of the distal end 22 of the cannula 12 into an eye. For example, the distal tip 22a may be beveled, sharpened, or otherwise shaped or structured to facilitate insertion of the cannula 12 into an eye without slippage or undue force.

It is desirable, although not necessary, that the cannula 12 corresponds in dimensions to a 21 or 22 gauge needle, and more preferably, an even smaller gauge needle. In one aspect of the invention, the cannula 12 has an outside diameter no larger than a 22 gauge needle. For example, the cannula may have a diameter equal to a 27 gauge needle. For example, the cannula 12 may have an outer diameter equal to or smaller than that of a thin-walled or ultra thin-walled 25 or 27 gauge needle.

In some embodiments the cannula lumen has a diameter of less than about 350 microns, or less than about 300 microns, or less than about 250 microns. In a specific embodiment, the cannula is a 25 gauge needle having a lumen with a diameter of 262 microns or 312 microns. In another specific embodiment, the cannula is a 27 gauge needle having a lumen with a diameter of 210 microns or 287 microns.

Such a small gauge cannula has the important advantage that punctures made by such small gauge cannula according to techniques described herein are self-sealing. A 21 gauge or 22 gauge needle is currently considered state of the art, and insertion of an implant using such a needle size does not always result in a wound that is self-sealing. The present invention preferably comprises a cannula or needle that has a smaller gauge or a smaller outer diameter than the 21 gauge or 22 gauge needle, such that implant delivery into the eye using the present invention is usually self sealing and can be accomplished without the need for suturing the puncture site. By using a cannula that has a gauge or an outer diameter smaller than a 21 gauge or 22 gauge cannula or needle, the implant can be placed and the cannula withdrawn without excessive fluid leakage from the eye, despite the normal fluid pressures within the eye, and stitching of the puncture site can be avoided. 21 gauge needles have outer diameters of about 0.032 inches (about 813 microns). Thin wall or extra or ultra thin wall versions of 21 gauge needles can have lumen diameters of about 0.023 inches (about 585 microns) to about 0.026 inches (about 610 microns). 22 gauge needles have outer diameters of about 0.028 inches (about 711 microns), and thin wall or extra or ultra thin wall versions of 22 gauge needles have lumen diameters of about 0.019 inches (about 483 microns) to about 0.023 inches (about 585 microns). Preferably, the cannula of the present assemblies has dimensions no larger than the dimensions of 22 gauge or 23 gauge, thin wall needle. Even more preferably, the cannula of the present assemblies has dimensions corresponding to those of a 25 gauge or 27 gauge, thin wall or extra or ultra thin wall needle.

Further, the ocular or intraocular implant 40 located in the cannula 12 is preferably structured with sufficient tolerance to be readily pushed through the lumen 14. For example, and without being so limited, the ocular implant in a cannula having dimensions corresponding to a lumen of a 22 gauge thin wall needle may comprise a plurality of a implants or particles having diameters of about 0.018 inches (about 460 microns). As another example, an implant having a diameter of 0.015 inches (about 380 microns) is suitable for delivery through a cannula having dimensions corresponding to 23 gauge thin wall needle. Implants sized for delivery through a cannula having dimensions corresponding to a 25 or 27 gauge thin wall or extra or ultra thin wall needle may also be employed.

The invention further contemplates that the cannula 12 may have a circular cross-section or a non-circular cross-section, including for example and without limitation, an oval or elliptical cross-section. For such a non-circular cross-sectional cannula, it is desirable that the cross-sectional area correspond to that of a circular cannula having up to about a 0.032 inch (813 microns) outer diameter, that is, a cross-sectional area up to about 0.0008 square inches (0.52 square millimeters) or more, depending on the particular cross-sectional geometry being employed.

In addition to cannula dimensions, additional modifications to both the cannula distal tip 22a and/or methods of insertion can further aid successful self-sealing methods of implantation. A typical problem when inserting a cannula into any tissue is the phenomena of "coring" of the tissue, where the insertion actually cuts a cylindrical section of tissue that enters the cannula lumen. Such coring when it occurs in the eye can exacerbate leakage of eye fluid through the injection site. By approaching the eye tissue at more of an angle relative to normal, there is a better opportunity for the cannula distal tip to penetrate and separate through the tissue layers and reduce coring of the tissue.

The cannula distal tip 22a itself also can be configured to reduce the coring phenomena, for instance, by providing that the tip is beveled, and/or by sharpening certain portions of the tip and dulling others. One skilled in the art will appreciate that the particular site of entry and the distance the cannula 12 is inserted will depend on the particular application and the desired final location of the implant. As can also be appreciated, the ability provided herein to provide for a self-sealing method for delivering implants has enormous impact on the ability of physicians and healthcare workers to treat diseases of the eye, because it obviates in most situations the necessity of surgery facilities, and accompanying surgical support, currently required by conventional apparatus and methods.

In one aspect of the invention, the diameter of the lumen 14 is in a range of about 200 microns or less to about 500 microns or more. The diameter of the lumen 14 may be about 350 microns or less, and may be in a range of about 250 microns to about 300 microns.

Referring now specifically to FIG. 1, the distal closure element 32 covers the distal end 22 and the distal end opening 24 of the cannula 12. For example, the distal closure element 22 may be of any suitable composition, shape or form that enables the distal closure element 22 to be removably engaged to the distal end 22 of the cannula 12.

The distal closure element 22 may be self secured to the cannula 12. For example, the distal closure element 22 may comprise a flexible polymeric material, for example, selected from flexible silicone polymeric materials, other flexible, for example, thermoplastic, polymeric materials and the like and combinations thereof, that enables the distal closure element 22 to be frictionally engaged to or secured to the distal end of the cannula. Alternatively, the distal closure element 22 may be adhesively secured to the cannula 12. In any event, it is preferable that the distal closure element 22 is structured to be effective in sealing the distal opening 24 of the cannula 12, for example, in a fluid tight manner.

Still referring to FIG. 1, the proximal closure element 36 is positioned in or substantially directly adjacent the proximal end opening of the cannula 12 and is preferably positioned to sealingly close, meaning, for example, in a fluid tight manner, the proximal end opening 18 of the cannula. Like the distal closure element 32, the proximal closure element 22 may comprise a polymeric material, for example, a flexible polymeric material, such as a material selected from flexible silicone polymeric materials, other flexible, for example, thermoplastic, polymeric materials and the like and combinations thereof. Preferably, the proximal closure element 36 is structured to be manually removable from the cannula 12, for example, prior to using the cannula in delivering the contained implant into an eye.

In an especially advantageous embodiment, the assembly 10 further comprises an enlarged sleeve 48 coupled to the cannula 12 and extending proximally thereof. The sleeve 48 is structured and positioned to facilitate coupling of the cannula 12 to a syringe (not shown in FIGS. 1 and 2) or other mechanism useful for injecting the implant 40 from the cannula 12 and into a region of an eye.

As shown in FIGS. 1 and 2, the sleeve 48 is structured and positioned to facilitate the sealing of the proximal end opening 18 of the cannula 12 by the proximal closure element 36. For example, referring now to FIG. 2, the proximal closure element 36 includes a distal region 36a that is shaped and sized to be received into, for example, press fit into, a corresponding channel or cavity 48a of sleeve 48. When the proximal closure element 36 is properly engaged with the sleeve, such as shown in FIG. 1, a sealing surface 36b of the proximal closure element 36 substantially entirely covers and seals, preferably in a fluid tight manner, the proximal end opening 18 of the cannula 12.

Turning now to FIG. 3, the assembly 10 is shown having the proximal closure element 36 (shown in FIGS. 1 and 2) removed therefrom, and the sleeve 48 of assembly 10 being used to facilitate coupling of the cannula 12 to a syringe 50 which will be used to inject the implant 40 into a region of an eye. In this example, the syringe 50 is a standard syringe 50 having a barrel 52 having a hub 54, and a plunger 56.

To use the assembly 10 to place the implant 40 into a region of an eye, the following procedure may be followed. An appropriate amount of sterile carrier fluid 62 is drawn into the barrel 52 of syringe 50, for example, using the plunger 56. Air trapped in the barrel between the plunger and a distal opening of the hub is removed in a conventional manner. The proximal closure element 36 is removed from the cannula 12. The hub 52 of the syringe 50 is press fit, threaded, or otherwise engaged to the sleeve 48 of the assembly 10. The distal closure element 32 is removed from the cannula 12 to expose the distal tip 22a. The syringe 50 and assembly 10 are then used to place the implant 40 into a region of an eye by accessing the target area within the ocular region with the distal end 22 of the cannula 12. Once the distal end 22 of the cannula 12 is within the target area, e.g., the vitreous cavity, the plunger 56 can be depressed to drive or force the fluid and the implant distally. As the plunger is moved distally or forward, it pushes the implant 40 into the target area (i.e. the vitreous) of the eye.

As a specific example, for placement e.g. in the vitreous cavity of the eye, useful implantation methods include advancing the cannula through the pars plana at a location about 3.5 to about 4 mm from the limbus of the eye. For smaller diameter cannulas, e.g., 25 gauge or smaller, the cannula can be inserted from any angle relative to the eye and still produce acceptable self-sealing results. For larger gauge cannulas, e.g., 23 gauge and larger, self-sealing results can be enhanced by inserting the cannula or needle at an angle, for example, other than perpendicular, relative to the eye surface. For example, good results are achieved by inserting the cannula or needle at an angle of about 45° or less relative to the eye surface. Also, slightly improved results can be seen in some cases by orienting the bevel of the needle downward with respect to the eye surface. Another advantageous method involves a so-called "tunnel technique" approach. In this technique, the patient's eye is restrained from moving e.g. using a cotton swab or forceps, and the needle is advanced into the sclera at an angle approaching parallel relative to the eye surface. In this technique, the bevel will usually be oriented upward with respect to the eye surface. Once the tip is advanced sufficiently far enough into the scleral layer, usually such that the bevel portion is at least disposed within the scleral layer, the angle of the needle is adjusted to a more downward angle into the eye, and the needle is further advanced. Using such methods, with the shallower angle of insertion, yields wound edges that close up and seal more readily. Without being bound by theory, it is believed that insertion of the needle by this technique creates a scleral "flap" that, under intraocular pressure of the eye, is forced upward and pressed against the wound path to more effectively close up the wound.

In addition, the direction of insertion of the needle relative to the limbus of eye can have further implications upon the deposition of the implant in the vitreous cavity. For example, advancement of the cannula posteriorly of the limbus or even circumferentially relative to the limbus usually provides for a suitable and acceptable location for deposition of the implant.

The implants may have a size in a range of about 5 µm to about 10 mm or greater, or about 10 µm to about 1 mm or about 3 mm per particle. The implants may have any appropriate length so long as the diameter of the implant permits the implant to move through the needle or cannula, and the length of the implant does not exceed the length of the cannula.

Figure 5:
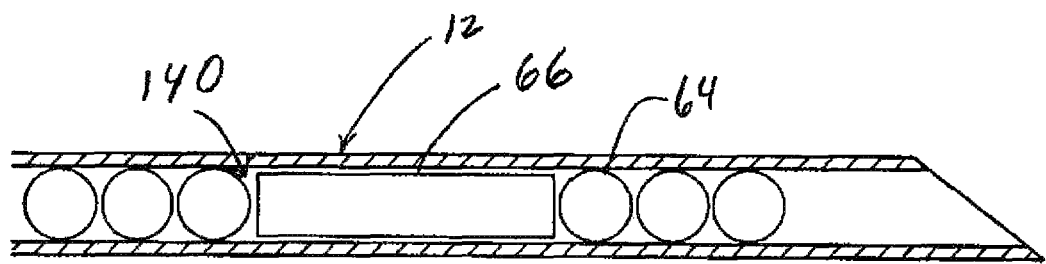
FIG. 5 is an enlarged cross sectional view of a distal portion of a cannula containing another form of an ocular implant useful as a component of the assemblies of the present invention.
Figure 6:
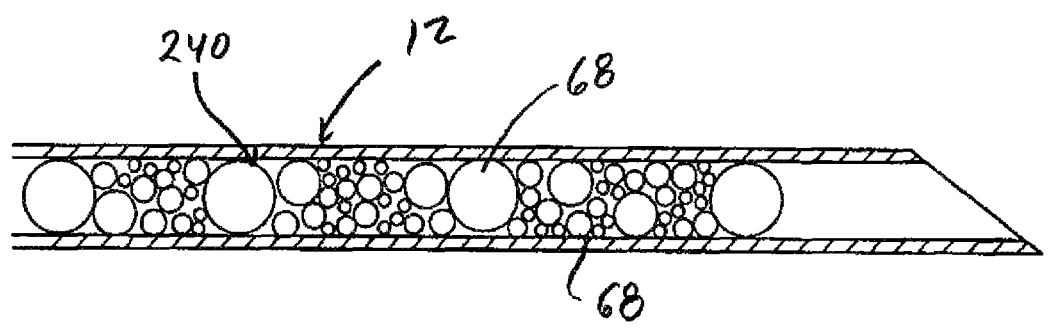
FIG. 6 is an enlarged cross sectional view of a distal portion of a cannula containing yet another form of an ocular implant useful as a component of the assemblies of the present invention.

The implants located in the cannula may have various forms. Turning now to FIGS. 4-6, several different implant forms, in accordance with the invention, are shown. FIG. 4 illustrates a magnified view of implant 40 located in the cannula 12, the implant 40 being comprised of a plurality of substantially uniformly sized microspheres 64. For example, the plurality of particles includes a smallest particle and a largest particle having a maximum transverse dimension within about 20%, preferably within about 10%, and more preferably within about 5%, of the maximum transverse dimension of the smallest particle.

Production of uniformly sized particles may be achieved by conventional techniques, such as sieving and the like, that are effective to separate, from a large number of non-uniformly sized particles, a plurality of particles of substantially uniform size. In one embodiment, and preferably, the production of uniformly sized microspheres is accomplished using microfluidic techniques for producing "precision" microparticles. Examples of such techniques are described in Barrow et al., United States Patent Application Publication No. 2006/0108012, published on May 25, 2006.

The plurality of particles located in the lumen 14 may include any suitable number of particles, for example and without limitation, in a range of about 5 or less or about 10 or about 25 to about 75 or about 100 or about 150 or about 200 or more particles.

FIG. 5 shows another type of ocular or intraocular implant, identified generally as 140, located in cannula 12 and useful in the present assemblies. Implant 140 comprises at least one cylindrical pellet (e.g., rod-shaped particle or rod 66) and a plurality of substantially uniformly sized microspheres 64 on either side of cylindrical pellet 66.

FIG. 6 shows yet another type of ocular or intraocular implant, identified generally as 240, located in cannula 12 and useful in the present assemblies. Implant 240 comprises a plurality of microspheres 68 which have different diameters.

Figure 7:
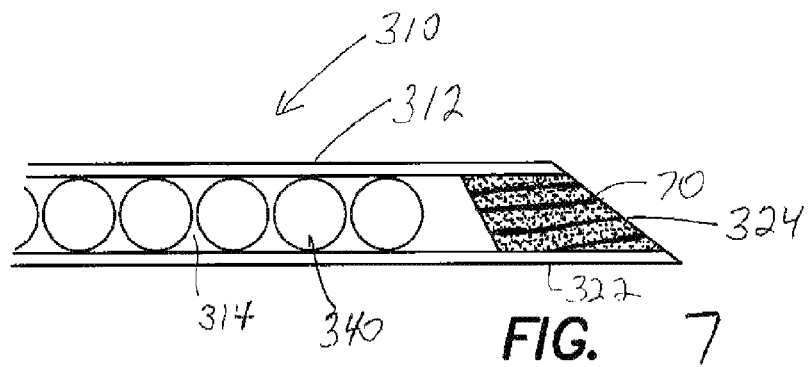
FIG. 7 is a partial cross-sectional view of a further assembly in accordance with the present invention.

With reference now to FIG. 7, a further embodiment of an assembly in accordance with the present invention is shown. Except as expressly described herein, this further embodiment, shown as assembly 310, is structured and functions similarly to assembly 10. Components of further assembly 310 which correspond to components of assembly 10 are identified by the same reference numeral increased by 300.

The primary difference between further embodiment 310 and embodiment 10 is the presence of distal seal plug 70, which may be used with or without the removable distal closure element 32. In one very useful embodiment the distal seal plug 70 is used instead of the removable distal closure element. The distal seal plug 70 functions to seal the distal end opening 324 of cannula 312 of assembly 310 to prevent the implant 340 from passing through the distal opening 324 unintentionally. In addition, the distal seal plug 70 advantageously seals the distal end opening 324 so that no fluid can enter or exit the lumen 314 of cannula 312 through distal end opening 324 when the distal seal plug is in place sealing the distal end opening, as shown in FIG. 7.

The distal seal plug 70 may be made of any suitable material, for example and without limitation, a polymeric material. The plug material is preferably anhydrous so that it does not impart or transfer any water (moisture) to the implant. Additionally the plug material is preferably rapidly bioerodible or biodegradable and can therefore be a suitable material, for example and without limitation, selected from poly(esters) based on polylactide (PLA), polyglycolide (PGA), polycaprolactone (PCL), and their copolymers, as well as poly(hydroxyalkanoates) of the PHB-PHV class, additional poly(esters), other synthetic polymers and natural polymers, particularly, modified so as to be rapidly biodegradable. In one embodiment, poly(saccharides), e.g., starch, cellulose, cellulose or cellulosic derivatives, such as HPMC and the like materials compatible with the eye and chitosan can form the plug material.

Although the distal seal plug 70 can be removed from the cannula 312 prior to the assembly 310 being used to implant the ocular implant 340 in an eye, in one useful embodiment, the distal seal plug is structured to be passed into the eye with the implant. In this latter embodiment, the distal seal plug 70 advantageously comprises a biodegradable or bioerodible polymeric component. Thus, as the implant 340 is being urged distally in the cannula 312, for example, by a syringe or push-rod device, the urging force also urges the distal seal plug distally. With the distal end 322 of cannula 312 in the eye, the distal seal plug 324, as well as the implant 340, are deposited in the eye.

In one embodiment the distal seal plug 70 is formed by coating the distal end opening 324 of cannula 312 with a fluid polymeric component, for example, a molten polymeric component, a polymeric component in an aqueous solution and the like. After such coating, the polymeric component is allowed to solidify, forming the distal seal plug 70. The polymeric component and the structure of the distal seal plug may be selected to provide a distal seal plug which functions as described herein and can be urged into an eye by the force generated by a syringe or push-rod device coupled to assembly 310.

In one useful embodiment, the polymeric component employed in the distal seal plug 70 may be, for example and without limitation, cellulosic polymers, such as HPMC, polyesters, such as PLGA, and the like and combinations thereof.

Figure 8:
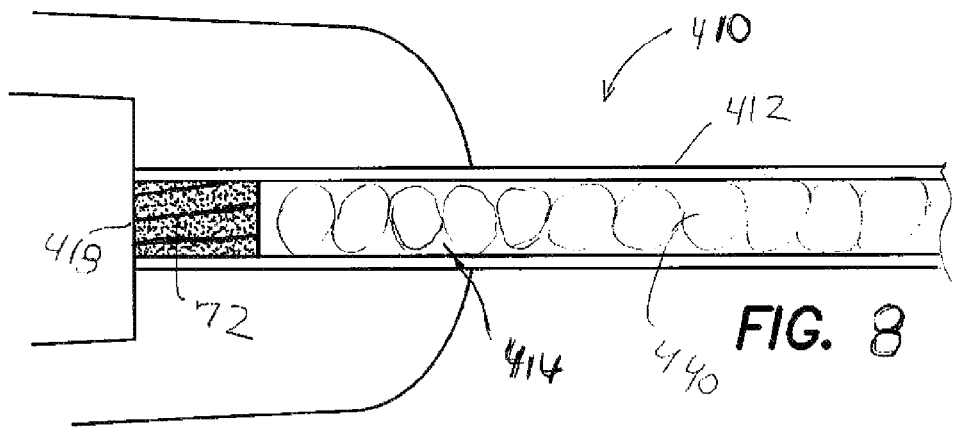
FIG. 8 is a partial cross-sectional view of an additional assembly in accordance with the present invention.

Now, with reference to FIG. 8, an additional embodiment of an assembly in accordance with the present invention is shown. Except as expressly described herein, this additional embodiment, shown as assembly 410, is structured and functions similarly to assembly 10. Components of additional assembly 410 which correspond to the embodiments of assembly 10 are identified by the same reference numeral increased by 400.

The primary difference between further between additional embodiment 410 and embodiment 10 is the presence of a proximal seal plug 72 which may be used with or without the removable proximal closure element 36 and with or without the removable distal closure element 32 and/or the distal seal plug 70. In one very useful embodiment, the proximal seal plug 72 is used instead of the removable proximal closure element 36.

The proximal seal plug 72 functions to seal the proximal end opening 418 of cannula 412 of assembly 410 to prevent the implant 440 from passing through the proximal opening 418 unintentionally. In additional, the proximal seal plug 72 advantageously seals the proximal end opening 418 so that no fluid can enter or exit the lumen 414 of cannula 412 through proximal end opening 418 while the proximal seal plug is in place sealing the proximal end opening, as shown in FIG. 8. The proximal seal plug 72 may be made of any suitable material, for example and without limitation, a polymeric material. Examples of suitable materials for use in proximal seal plug 72 include, without limitation, the materials from which distal seal plug 70 can be made, as described elsewhere herein.

Although the proximal seal plug 72 can be removed from the cannula 412 prior to the assembly 410 being used to implant the ocular implant 440 in an eye, in one useful embodiment, the proximal seal plug is structured to be passed into the eye with the implant. In this latter embodiment, the proximal seal plug 72 advantageously comprises a biodegradable or bioerodible component, for example and without limitation, a biodegradable or bioerodible polymeric component. Thus, as the implant 440 is being urged distally in the cannula, for example, by a syringe or push-rod device, the urging force also urges the proximal seal plug 72 distally through the distal end opening of cannula 412 in the eye. Thus the proximal seal plug 72, as well as the implant 440 are deposited in the eye.

In one embodiment, the proximal seal plug 72 is formed by coating the proximal end opening 418 of cannula 412 with a fluid polymeric component, for example a molten polymeric component, a polymeric component in an aqueous solution and the like. After such coating, the polymeric component is allowed to solidify forming the proximal seal plug 72. The polymeric component and the structure of the proximal seal plug 72 may be selected to provide a distal seal plug or a proximal seal plug 72 which functions as described herein and can be urged into the eye by the force generated by a syringe or push-rod device coupled to assembly 410. The polymeric component employed in the proximal seal plug 72 may be, for example and without limitation, selected from a cellulosic polymers, such as HPMC, polyesters such as PLGA, and the like and combinations thereof.

With reference now to FIGS. 9 to 14, an alternate embodiment of an assembly in accordance with the present invention is shown. Except as expressly described herein, this further embodiment, shown as assembly 510, is structured and functions similarly to assembly 10. Components of alternate assembly 510 which correspond to components of assembly 10 are identified by the same reference numeral increased by 500.

Figure 9:
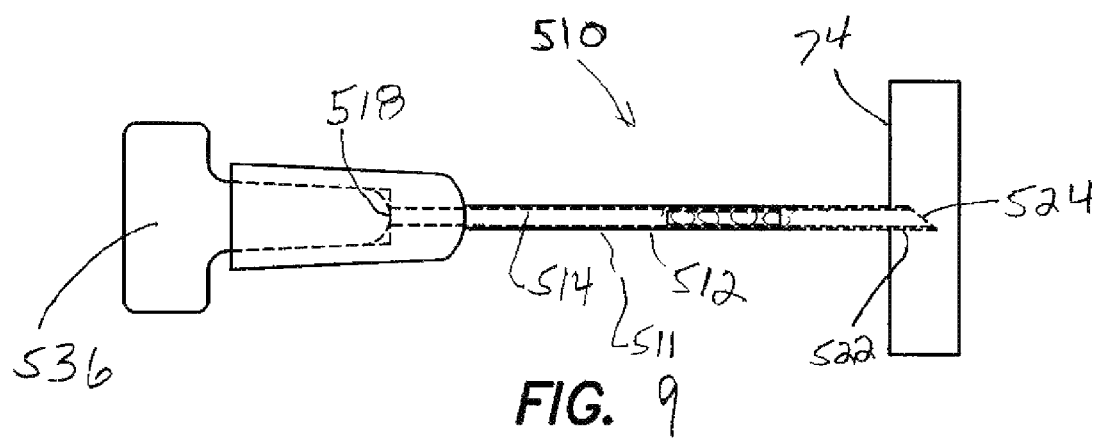
FIG. 9 is a cross-sectional view of an alternate assembly in accordance with the present invention.

The primary difference between alternate embodiment 512 and embodiment 10 is the presence of a distal cap 74 to cover the distal end 522 and distal opening 520 of cannula 512 of assembly 510. In addition, the distal cap 74 advantageously seals the distal end opening 524 so that no fluid can enter or exit the lumen 514 of cannula 512 through distal end opening 524 when the distal cap is in place sealing the distal end opening, as shown in FIG. 9.

This distal cap 74 may be made of any suitable material, for example and without limitation, a polymeric material, effective to provide a cap which is structured and functions as described herein. In one embodiment, the distal cap is made of flexible, for example and without limitation, thermoplastic, polymeric material. In a very useful embodiment, the distal cap comprises a flexible, silicone polymeric material. The distal cap can be a single solid piece of silicone polymeric material. In one embodiment, the distal cap may be opaque or substantially translucent or substantially transparent, for example, clear or optically clear. Using a substantially transparent or clear distal cap may allow the operator to visualize the cannula so as to at least assist in determining where the cannula tip is located as it is being placed in the eye. The distal cap may, and advantageously does, have sufficient softness to be pierced by the cannula 512 of the assembly 510 in passing the cannula into an eye without significantly detrimentally effecting the cannula or the eye into which the cannula is passed. The distal cap 74 advantageously has a durometer in a range of about 30 to about 75. Such a relatively soft distal cap 74 is effective in receiving the distal end 522 and distal end opening 524 of the cannula 512 of alternate assembly 510 without requiring the provision of a separate bore in the distal cap. The distal cap 74 is advantageously configured or structured and formulated to remain securely in place covering the distal end 522 and distal opening 524 of cannula 512 which the assembly 510 is being shipped and stored; to be pierced by the distal end 522 of the cannula 512 as the cannula is moved distally toward an eye, for example, without significantly detrimentally affecting the sharpness of the cannula and/or its ability to pass into an eye; and/or to move proximally on the cannula 512 as the distal end 522 is inserted in the eye.

In one useful embodiment, the distal cap 74 has a generally disc-like shape, for example, a generally circular disc-like shape. In this embodiment, the distal cap has a diameter, for example, and without limitation, in a range of about 4 mm or about 5 mm to about 8 mm or about 10 mm, and a thickness, for example and without limitation, in a range of about 1 mm to about 2 mm or about 3 mm.

One advantage of having a distal cap 74 with an 8 mm diameter is that the operator, by positioning the edge of the cap towards the limbus of the eye, is provided with a quick 4 mm measurement from the limbus. That is, with the edge of the cap toward the limbus of the eye, the distal end of the cannula is 4 mm or about 4 mm from the limbus. The operator does not have to use a caliper to pre-measure the distance to the limbus. At 4 mm from the limbus, the operator can safely and effectively insert the implant through the pars plana into the vitreous cavity. With a thickness in a range of about 1 mm to about 2 mm, the distal cap 74 can be securely placed over the distal end of a cannula, for example, a 25 gauge, ultra thin walled X ⅝ inch.

In one embodiment, the cap may be provided with markings or graduations at different radial distances from the cannula indicating the distance of the individual marking or graduation from the cannula. For example, the markings or graduations can be on a millimeter scale or smaller distance increments so that the operator can measure the distance between a given point on the eye, for example the limbus of the eye, and the cannula tip so as to insert the cannula tip at a desired point into the eye. This embodiment is useful, for example, if the cap has an 8 mm diameter and the surgeon chooses to go 3 mm from the limbus for a pars plana injection. Thus, by placing the 3 mm marking or graduation of the cap on or in proximity to the limbus, the operator has also placed the cannula tip at the desired injection region. Using a cap with such markings or graduations also allows the operator to avoid using a caliper to pre-measure the 3 mm distance from the limbus.

Advantageously, the distal cap 74 remains associated with the cannula 512 as the implant 540 is implanted into an eye.

It should also be noted that a proximal closure element 536 is used to close an preferably seal the proximal end opening 518 of assembly 510. A proximal seal plug, such as proximal seal plug 72, may be used in combination with or in place of proximal closure element 536, as described herein.

Figure 10:
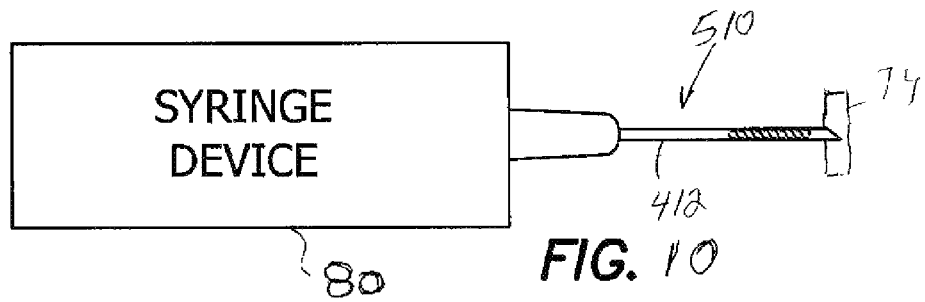
FIG. 10 is a somewhat schematic view of the capped cannula of the assembly of FIG. 9 shown coupled to a syringe device.

FIG. 10 shows cannula 512 with cap 74, located on the distal end of the cannula joined to a syringe device 80.

Figure 11:
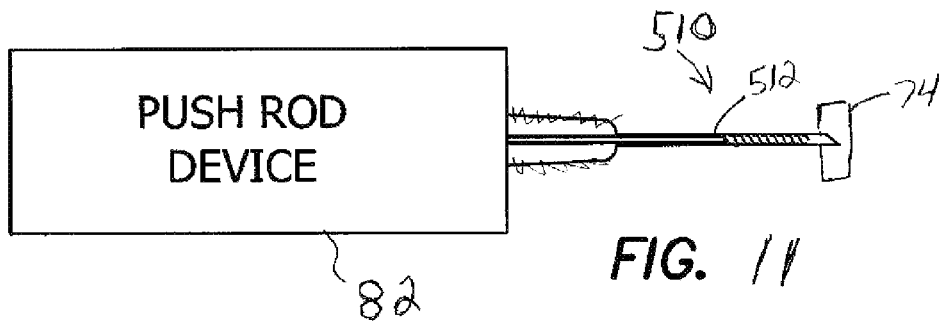
FIG. 11 is a somewhat schematic view of another assembly in accordance with the present invention shown coupled to a push-rod device.

FIG. 11 shows an assembly 510 without a sleeve joined directly to a conventional push-rod device 82.

Both the syringe device 80 and push-rod device 82 are of conventional design and structure and are used to provide or apply a force to the lumen of cannula 512 to urge the implant 540 into the eye.

Figure 14:
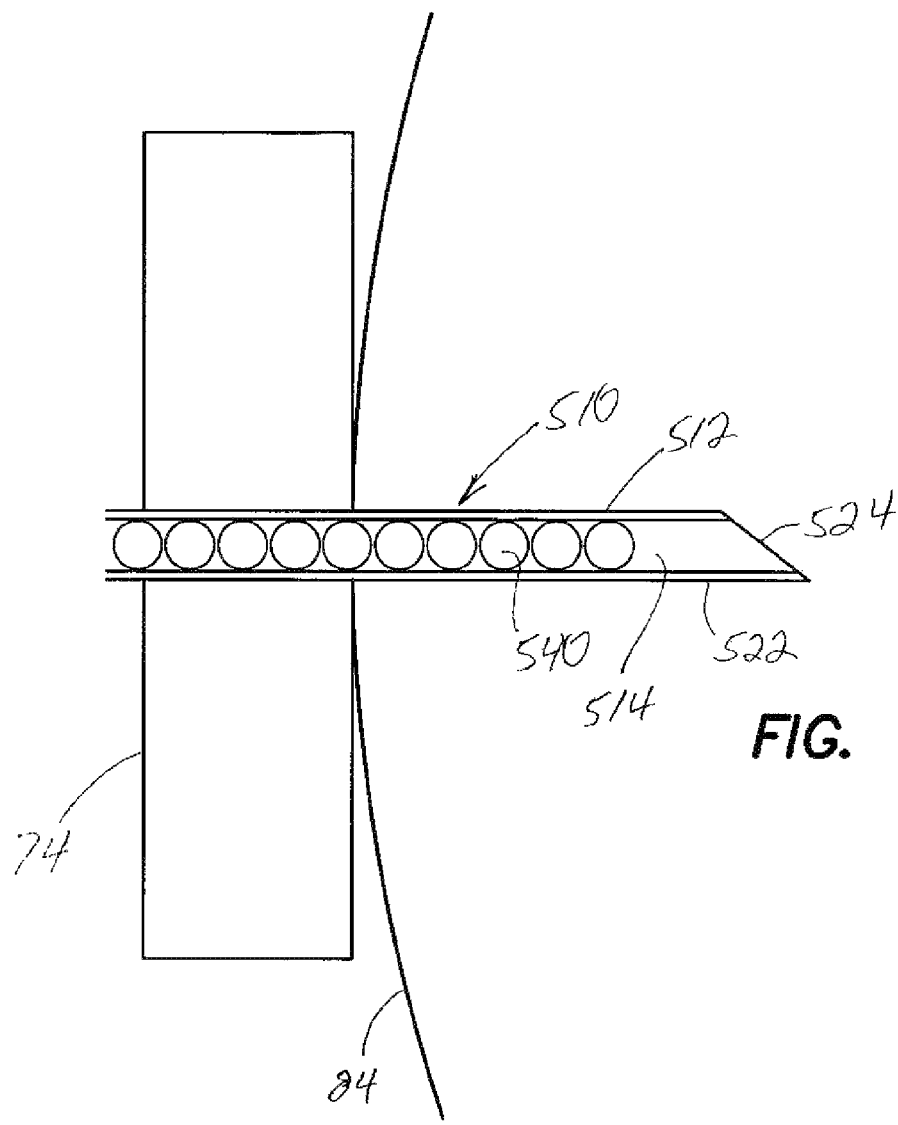
FIG. 14 is a cross-sectional view of a portion of the cannula of the assembly of FIG. 11 shown with a larger portion of the cannula located inside an eye.
Figure 12:
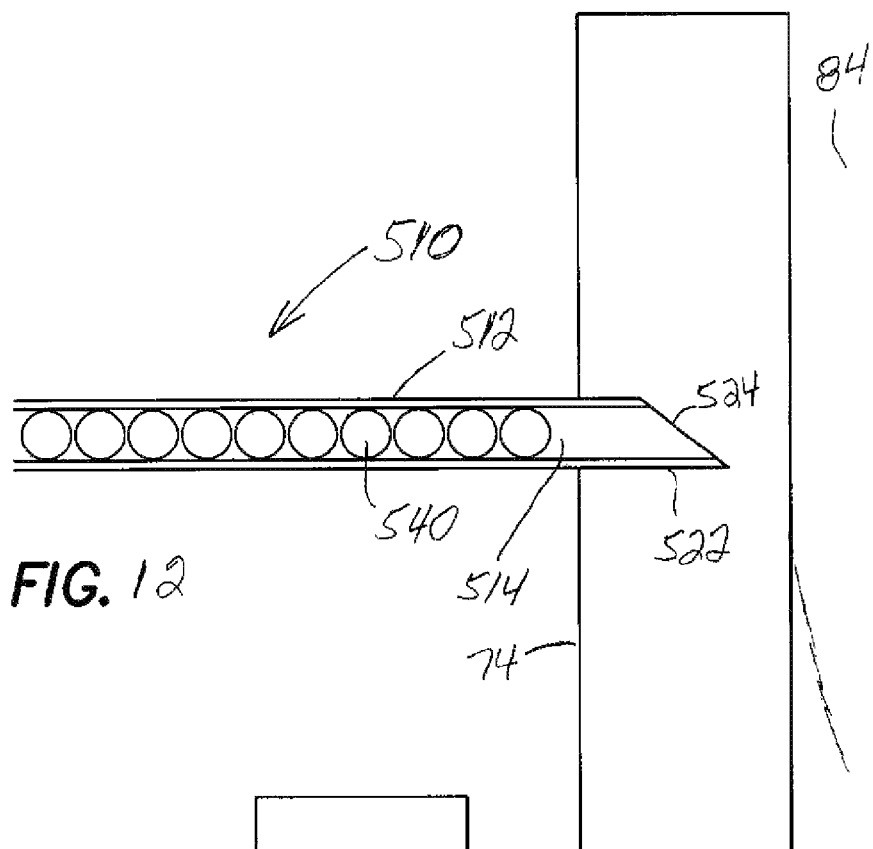
FIG. 12 is a cross-sectional view of a portion of the capped cannula of the assembly of FIG. 11 shown with the cannula ready to be passed into an eye.
Figure 13:
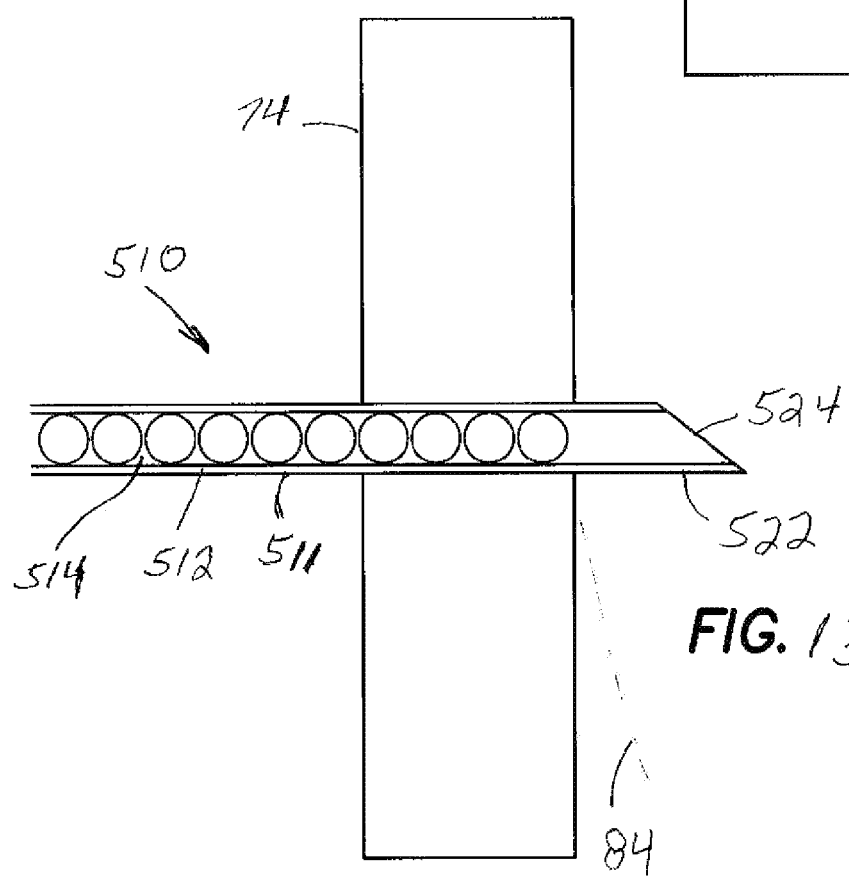
FIG. 13 is a cross-sectional view of a portion of the capped cannula of the assembly of FIG. 11 shown with a small portion of the cannula located inside an eye.

FIGS. 12, 13 and 14 illustrate more clearly the interaction between the cannula 512, the cap 74 and the surface 84 of an eye into which the implant 540 is to be placed. With specific reference to FIG. 12, the assembly 510, attached to either a syringe 80 or a push-rod device 82 (not shown in FIG. 12, 13 or 14) is placed against the surface 84 of the eye. The assembly 510 is urged distally. Such urging causes the distal end 522 and distal end opening 524 of the assembly 510 to pass distally through the distal cap 74 through the surface 84 and into the eye. The position of the cannula 512 after the distal end 522 and distal end opening 524 are in the eye is shown in FIG. 13. One important aspect of the present invention is that the cap 78 moves proximally along the outer surface 511 of the cannula 512 so that the further the cannula is passed into the eye, the cap moves more proximal on the cannula.

FIG. 14 shows the position of the cap 74 as the distal end 522 of the cannula 512 is moved further into the eye. The cap 74 has moved further proximally on the cannula 512.

The position of the cap 74 on the cannula provides the operator with a direct visualization of how much of the cannula is placed in the eye. This gives the operator an additional control for judging the progress of the procedure.

Once the cannula is in the proper position in the eye, the syringe or push-rod assembly is activated to urge the implant 540 into the eye. After the implant 540 has been delivered in the eye, the cannula is removed from the eye.

Generally, the particles or microparticles making up the ocular or intraocular implants 40, 140, 240, 340, 440 and 540 should have a diameter that is less than the diameter of the lumen 14 of the cannula 12. In one embodiment, the maximum transverse dimension of each particle of the plurality of particles is about 70% of the diameter of the lumen, for example, is about 80% of the diameter of the lumen, for example, is about 90% of the diameter of the lumen. Smaller particles, for example in combination with relatively larger particles, may also be employed.

In certain implants, the particle diameter is less than about 500 µm, for example, is less than about 350 µm. The vitreous chamber in humans is able to accommodate relatively large implants of varying geometries, having lengths of, for example, about 1 to about 10 mm. Rod shaped particles 64 may have dimensions of about 2 mm length or about 7 mm to about 10 mm length by about 0.75 mm to about 1.5 mm. diameter.

Advantageously, because the implants 40, 140, 240, 340, 440 or 540 are made up of separate particles, such implants are generally more flexible than implants made up of a single uniform structure. This feature of the invention greatly facilitates both insertion of the implant in the eye, such as in the vitreous, and accommodation of the implant. As shown, each of implants 40 and 140 may comprise a plurality of particles disposed in a one-by-one (synonymously, in a single file manner) array along the length of the lumen.

The total weight of the implant is often in a range of about 250 to about 5000 µg, for example, about 500 to about 1000 µg. An implant may be about 500 µg, or about 1000 µg. For non-human individuals, the dimensions and total weight of the implant(s) may be larger or smaller, depending on the type and size of the individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or for example, about 26 times larger for an implant for an elephant.

Implants 40, 140, 240, 340, 440 and 540 can be prepared where all or some of the particles are made of one material having a single outer surface and/or may have one or more layers of the same composition or different compositions, where the layers may be of cross-linked and/or uncross-linked polymeric materials, or of materials having different molecular weights, different densities, different porosities, and the like. Such particles may be structured and/or formulated to alter, and preferably control, the release rate or profile of a drug from the implant. For example, where it is desirable to quickly release an initial bolus of drug, the center of a particle may include a polylactate coated with a polylactate-polyglycolate copolymer, so as to enhance the rate of initial degradation. Alternatively, the center may include a water soluble polymer, such as polyvinyl alcohol and the like, coated with a polylactate, so that upon degradation of the polylactate exterior the center would dissolve and be rapidly washed out of the eye.

Although not shown, it is to be appreciated that the implants suitable for use in the present assemblies may be of particles having geometries or forms other than rods and spheres. Such other geometries or forms include, but are not limited to fibers, sheets, films, cubes, ellipsoids, discs, plaques and the like.

The upper limit for the particle size will be determined by factors such as toleration for the particle, the size of the target area of the eye, size limitations on insertion, ease of handling, etc. Where sheets or films are employed, the sheets or films may be at least about 0.5 mm by about 0.5 mm, usually in a range of about 3 to about 10 mm by about 5 to about 10 mm, with a thickness in a range of about 0.1 to about 1.0 mm for ease of handling. Where fibers are employed, the fiber diameter will generally be in the range of about 0.05 to about 3 mm and the fiber length will generally be in the range of about 0.5 to about 10 mm. Ellipsoids may be in the range of about 0.5 µm to 4 mm along the major and minor axes thereof, with comparable volumes for other shaped particles.

The present assemblies may include substantially no liquid material in the lumen with the implant. For many types of implants having certain compositions, by maintaining the implant in a dry state the implant will have an extended storage life.

In other embodiments of the invention, the assemblies further comprise a carrier medium, more specifically, a flowable carrier medium, located in the lumen with the implant, for example, sealed in the lumen with the implant.

It is to be appreciated that the suitable carrier media described herein are, in many instances, suitable for use as pushing fluids, or pushing gels, as described elsewhere herein, for example, with such pushing fluids or gels being contained in a syringe to be coupled to the present cannulas containing the implants. For example, in some assemblies of the invention in which the cannula contains an implant in dry form and the cannula is structured to be coupled to a syringe containing a pushing fluid, the pushing fluid may be made of the same or a similar material as the carrier medium as will now be described.

The carrier medium preferably is a composition that causes substantially no chemical or physical degradation or erosion of the implant for the period of time in which the implant is intended to be stored in the cannula. Preferably, the carrier medium functions at least in part as a lubricant to facilitate delivery of the implant from the lumen and into the eye. Depending on the composition of the implant and other factors such as biocompatibility, the carrier medium may be a saline solution, other aqueous based or alcohol based media, including, without limitation, flowable gels.

In a more specific embodiment, the carrier medium comprises an aqueous component and a viscosity inducing component. The viscosity inducing component is present in an amount effective in increasing the viscosity of the medium. Any suitable, preferably ophthalmically acceptable, viscosity inducing component may be employed in the assemblies of the present invention. Many such viscosity inducing components have been proposed and/or used in ophthalmic compositions used on or in the eye. Advantageously, the viscosity inducing component is present in an amount in a range of about 0.05% to about 20% (w/v) of the liquid medium. In one particularly useful embodiment, the viscosity inducing component is a hyaluronic acid component, such as sodium hyaluronate, other alkali metal hyaluronates and the like and mixtures thereof.

In one embodiment, the carrier medium has a viscosity of at least about 10 cps or at least about 100 cps, preferably at least about 1,000 cps, more preferably at least about 10,000 cps and still more preferably at least about 70,000 cps, for example, up to about 250,000 cps, or about 300,000 cps, at a shear rate of 0.1/second. It is to be appreciated that these measurements of viscosity refer to the viscosity of the medium generally at room temperature, which is in a range from about 20 degrees Celsius to about 25 degrees Celsius. The carrier media preferably have make-ups so as to be effectively, for example, manually, injected into a posterior segment of an eye of a human or animal, preferably through a 25 gauge needle, a 27 gauge needle, a 29 gauge needle or even a 30 gauge needle.

Any suitable viscosity inducing component, for example, ophthalmically acceptable viscosity inducing component, may be employed in accordance with the present invention. Many such viscosity inducing components have been proposed and/or used in ophthalmic compositions used on or in the eye. The viscosity inducing component is present in an amount effective in providing the desired viscosity to the composition. Advantageously, the viscosity inducing component may be present in an amount in a range of about 0.05% or about 0.5% or about 1.0% to about 5% or about 10% or about 20% (w/v) of the medium. The specific amount of the viscosity inducing component employed depends upon a number of factors including, for example and without limitation, the specific viscosity inducing component being employed, the molecular weight of the viscosity inducing component being employed, the viscosity desired for delivering the implants, including for example, factors such as shear thinning.

The viscosity inducing component preferably comprises a polymeric component and/or at least one viscoelastic agent, such as those materials which are useful in ophthalmic surgical procedures.

Examples of useful viscosity inducing components include, but are not limited to, hyaluronic acid (such as a polymeric hyaluronic acid), carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures and copolymers thereof.

The molecular weight of the presently useful viscosity inducing components may be in a range of about 10,000 Daltons or less to about 2 million Daltons or more. In one particularly useful embodiment, the molecular weight of the viscosity inducing component is in a range of about 100,000 Daltons or about 200,000 Daltons to about 1 million Daltons or about 1.5 million Daltons. Again, the molecular weight of the viscosity inducing component useful in accordance with the present invention may vary over a substantial range based on the type of viscosity inducing component employed, and the desired final viscosity of the medium in question, as well as, possibly one or more other factors.

In one embodiment, a viscosity inducing component is a hyaluronate component, for example, a metal hyaluronate component, preferably selected from alkali metal hyaluronates, alkaline earth metal hyaluronates and mixtures thereof, and still more preferably selected from sodium hyaluronates and mixtures thereof. The molecular weight of such hyaluronate component preferably is in a range of about 50,000 Daltons or about 100,000 Daltons to about 1.3 million Daltons or about 2 million Daltons. In one embodiment, the medium may include a hyaluronate component in an amount in a range about 0.05% to about 0.5% (w/v).

In a more preferred embodiment, the hyaluronate component is present in an amount in a range of about 1% to about 4% (w/v) of the medium. In this case, the high molecular weight hyaluronate component forms a gel, for example, an aqueous-based gel, that slows particle sedimentation rate to the extent that often no resuspension processing is necessary over the estimated shelf life, for example, at least about 1 year or at least about 2 years or longer, of the medium and implant contained in the cannula of the present assemblies. Such a medium is especially useful in the present assemblies since the gel cannot be easily removed by a needle and syringe from a bulk container. Pre-filled cannulas as described herein have the advantages of convenience for the injector and the safety which results from less handling.

The carrier medium is advantageously ophthalmically acceptable, that is substantially compatible with the eye and/or causes no undue or significant detrimental effect on the eye, and may include one or more conventional excipients useful in ophthalmic compositions. The present carrier media preferably include a major amount of liquid water. The present carrier media may be, and are preferably, sterile, for example, prior to being used in the eye.

Suitable carrier media may include one or more other components in amounts effective to provide one or more useful properties and/or benefits to the present assemblies. For example, the carrier medium may include effective amounts of a preservative component, preferably such components which are more compatible with or friendly to the tissue in the posterior segment of the eye into which the composition is placed than benzyl alcohol. Preferably, however, since the implant and carrier medium are advantageously sterilized and sealed in the cannula of the present assembly, preservatives are not used in or in conjunction with the implants or carrier media of the present invention. If preservatives are to be used, some that may be beneficial include without limitation, benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, is a concentration effective to preserve the implant and the carrier medium, and is often in a range of about 0.00001% to about 0.05% or about 0.1% (w/v) of the carrier medium.

If suitable, the carrier medium may further include an effective amount of resuspension component effective to facilitate the suspension or resuspension of the implant particles in the present assemblies. Such resuspension components are employed, for example, to provide an added degree of insurance that the implant particles remain in suspension, as desired and/or can be relatively easily resuspended in the carrier medium, if such resuspension is desired. Advantageously, the resuspension component employed in accordance with the present invention, if any, is chosen to be more compatible with or friendly to the tissue in the posterior segment of the eye into which the composition is placed than polysorbate 80.

Any suitable resuspension component may be employed in accordance with the present invention. Examples of such resuspension components include, without limitation, surfactants such as poloxanes, for example, sold under the trademark Pluronic®; tyloxapol; sarcosinates; polyethoxylated castor oils, other surfactants and the like and mixtures thereof.

One very useful class of resuspension components are those selected from vitamin derivatives. Although such materials have been previously suggested for use as surfactants in ophthalmic compositions, they have been found to be effective in the present invention as resuspension components. Examples of useful vitamin derivatives include, without limitation, Vitamin E tocopheryl polyethylene glycol succinates, such as Vitamin E tocopheryl polyethylene glycol 1000 succinate (Vitamin E TPGS). Other useful vitamin derivatives include, without limitation, Vitamin E tocopheryl polyethylene glycol succinamides, such as Vitamin E tocopheryl polyethylene glycol 1000 succinamide (Vitamin E TPGSA) wherein the ester bond between polyethylene glycol and succinic acid is replaced by an amide group.

The presently useful resuspension components are present, if at all, in the carrier media in accordance with the present invention in an amount effective to facilitate suspending the implant particles in the present carrier media, for example, during manufacture and thereafter. The specific amount of resuspension component employed may vary over a wide range depending, for example, on the specific resuspension component being employed, the specific implant particles and carrier medium with which the resuspension component is being employed and the like factors. Suitable concentrations of the resuspension component, if any, in the present carrier media are often in a range of about 0.01% to about 5%, for example, about 0.02% or about 0.05% to about 1.0% (w/v), of the carrier medium.

Without wishing to limit the invention to any particular theory of operation, it is believed that the use of relatively high viscosity carrier media, as described herein, provides for effective, and preferably substantially uniform, suspension of certain particulate implants.

For example, the implant may comprise a corticosteroid component present as a plurality of microparticles which are substantially uniformly suspended in the carrier medium. The particles may remain substantially uniformly suspended in the medium for at least about 1 week, preferably at least about 2 weeks or at least about 1 month, and still more preferably at least about 6 months or at least about 1 year or at least about 2 years, without requiring resuspension processing, that is, without requiring being shaken or otherwise agitated to maintain the corticosteroid component particles substantially uniformly suspended in the composition.

Implants comprising particles suspended in a carrier medium as described elsewhere herein provide such substantially uniform suspension of the particles, so as to be able to provide a consistent and accurate dose upon administration to an eye using the present assemblies. The assemblies thus provide substantial advantages relative to the prior art. In particular, the assemblies may be manufactured, shipped and stored for substantial periods of time without the implant particles precipitating from the carrier medium. Having the particles maintained substantially uniformly suspended in the carrier medium allows the assemblies to provide long term dosing consistency and accuracy per unit dose amount administered, without any need to resuspend the particles.

For some types of implants, it may be preferable to place the implant into a region of an eye without the use of a carrier fluid or carrier medium. For such purposes, a push-rod type activator device rather than syringe 50 may be used to drive the implant, for example, the implant stored in the cannula in a dry state, from the cannula without the use of a carrier medium.

It may be desirable to provide a relatively constant rate of release of the therapeutic component from the implant over the life of the implant. For example, it may be desirable for the therapeutic component to be released in amounts from about 0.01 µg to about 2 µg per day for the life of the implant. However, the release rate may change to either increase or decrease depending on the structure and/or formulation of the implant, for example and without limitation, the biodegradable polymer matrix of the implant. In addition, the release profile of the therapeutic component, that is the rate of release of the therapeutic component as a function of time, may include one or more linear portions and/or one or more non-linear portions. Preferably, the release rate is greater than zero once the implant has begun to degrade or erode.

The particles which make up the implant may be monolithic, i.e. having the active agent or agents homogenously distributed through the polymeric matrix, or encapsulated, where a reservoir of active agent is encapsulated by the polymeric matrix. Due to ease of manufacture, monolithic implants may be preferable over encapsulated forms. However, the greater control afforded by the encapsulated, reservoir-type implant may be of benefit in some circumstances, where the therapeutic level of the drug falls within a narrow window. In addition, the therapeutic component may be distributed in a non-homogenous pattern in the matrix. For example, the implant may include a portion that has a greater concentration of the therapeutic component relative to a second portion of the implant.

The size and form of the implant can also be used to control period of treatment and/or drug concentration at the site of implantation. Larger implants will deliver a proportionately larger dose, but, for example, depending on the surface to mass ratio, may have a slower release rate. The particular size and geometry of the implant are chosen to suit the site of implantation.

The proportions of the therapeutic component, matrix, and any other additives and/or modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is, after release, less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

The particles which make up the implants 40, 140, 240, 340, 440 and 540 preferably comprise a composition comprising a therapeutic component and matrix, for example, a polymeric component, for controlling release of the therapeutic component from the particle. Suitable polymeric materials or compositions for use in the polymeric components of the particles of the present invention include those materials which are compatible, that is, biocompatible, with the eye so as to cause no substantial interference with the functioning or physiology of the eye. Such materials preferably are at least partially and more preferably substantially completely biodegradable or bioerodible. Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cynao and amino. The polymers set forth in Heller, Biodegradable Polymers in Controlled Drug Delivery, In:CRC Critical Reviews in Therapeutic Drug Carrier Systems, Vol. 1, CRC Press, Boca Raton, Fla. 1987, pp 39-90, which describes encapsulation for controlled drug delivery, may find use in the present invention, and that disclosure is specifically incorporated herein by reference.

Of additional interest are polymers of hydroxyaliphatic carboxylic acids, either homopolymers or copolymers, and polysaccharides. Included among the polyesters of interest are polymers of D-lactic acid, L-lactic acid, racemic lactic acid, glycolic acid, polycaprolactone, and combinations thereof. Generally, by employing the L-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylecellulose esters characterized by being water insoluble, a molecular weight of about 5000 Daltons to about 500,000 Daltons, etc.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the particles suitable for use in the present invention may include biocompatibility, compatibility with the therapeutic component, ease of use of the polymer in making the implants of the present invention, a half-life in the physiological environment of at least about 6 hours, preferably greater than about one day, not significantly increasing the viscosity of the vitreous, and water insolubility.

The biodegradable polymeric materials which are included in the particles are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, where the polymers may be employed as varying layers or mixed.

The present implants advantageously are structured to have a lifetime at least equal to the desired period of therapeutic component administration in the eye, and may have lifetimes of about 5 to about 10 times the desired period of administration. The period of administration may be at least about 3 days, at least about 7 days, at least about 15 days, at least about 20 days, at least about 30 days, at least about 2 months, at least about 4 months, at least about 6 months, at least about 8 months, at least about 10 months, at least about 1 year or longer.

The therapeutic component useful in the implants may include any suitable pharmacologically active agent or therapeutic agent for which sustained release, for example, in the eye, is desirable. Advantageously, the therapeutic component is sufficiently soluble in region of the eye in which the implant is to be placed, for example, in the vitreous of the eye, such that it will be present at a pharmacologically or therapeutically effective dose. In some embodiments, the ocular implant may be of a make-up such that the implant is substantially insoluble in the carrier medium when contained in the lumen with the implant for example at room temperature, but is soluble when placed in the environment of the eye.

Pharmacological or therapeutic agents of interest include hydrocortisone (5-20 mcg/l as plasma level), gentamycin (6-10 mcg/ml in serum), 5-fluorouracil (about 0.30 mg/kg body weight in serum), sorbinil, IL-2, TNF, Phakan-a (a component of glutathione), thioloa-thiopronin, Bendazac, acetylsalicylic acid, trifluorothymidine, interferon (alpha., beta. and gamma.), immune modulators, e.g. lymphokines, monokines, and growth factors, etc. Pharmacological or therapeutic agents of particular interest include, without limitation, anti-glaucoma drugs, such as the beta-blockers, such as timolol maleate, betaxolol and metipranolol; mitotics, such as pilocarpine, acetylcholine chloride, isofluorophate, demacarium bromide, echothiophate iodide, phospholine iodide, carbachol, and physostigimine; epinephrine and salts, such as dipivefrin hydrochloride; and dichlorphenamide, acetazolamide and methazolamide; anti-cataract and anti-diabetic retinopathy drugs, such as aldose reductase inhibitors, such as tolrestat, lisinopril, enalapril, and statil; thiol cross-linking drugs other than those considered previously; anti-cancer drugs, such as retinoic acid, methotrexate, adriamycin, bleomycin, triamcinoline, mitomycin, cis-platinum, vincristine, vinblastine, actinomycin-D, ara-c, bisantrene, CCNU, activated cytoxan, DTIC, HMM, melphalan, mithramycin, procarbazine, VM26, VP16, and tamoxifen; immune modulators, other than those indicated previously; anti-clotting agents, such as tissue plasminogen activator, urokinase, and streptokinase; anti-tissue damage agents, such as superoxide dismutase; proteins and nucleic acids, such as mono- and polyclonal antibodies, enzymes, protein hormones and genes, gene fragments and plasmids; steroids, particularly anti-inflammatory or anti-fibrous drugs, such as cortisone, hydrocortisone, prednisolone, prednisome, dexamethasone, progesterone-like compounds, medrysone (HMS) and fluorometholone; non-steroidal anti-inflammatory drugs, such as ketrolac tromethamine, dichlofenac sodium and suprofen; antibiotics, such as loridine (cephaloridine), chloramphenicol, clindamycin, amikacin, tobramycin, methicillin, lincomycin, oxycillin, penicillin, amphotericin B, polymyxin B, cephalosporin family, ampicillin, bacitracin, carbenicillin, cepholothin, colistin, erythromycin, streptomycin, neomycin, sulfacetamide, vancomycin, silver nitrate, sulfisoxazole diolamine, and tetracycline; other antipathogens, including anti-viral agents, such as idoxuridine, trifluorouridine, vidarabine (adenine arabinoside), acyclovir (acycloguanosine), pyrimethamine, trisulfapyrimidine-2, clindamycin, nystatin, flucytosine, natamycin, miconazole and piperazie derivatives, e.g. diethylcarbamazine; cycloplegic and mydriatic agents, such as atropine, cyclogel, scopolamine, homatropine and mydriacyl; and the like and mixtures thereof.

Other agents useful in the systems of the present invention include, without limitation, anticholinergics, anticoagulants, antifibrinolytic agents, antihistamines, antimalarials, antitoxins, chelating agents, hormones, immunosuppressives, thrombolytic agents, vitamins, salts, desensitizing agents, prostaglandins, amino acids, metabolites, antiallergenics, and the like and mixtures thereof.

In some embodiments of the invention, the implants are suitable for treating inflammation-mediated conditions of the eye. The term "inflammation-mediated condition of the eye" is meant to include any condition of the eye which may benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic ophthalmia, Vogt Koyanagi-Harada (VKH) syndrome, histoplasmosis, and uveal diffusion.

For example, the implant may comprise a plurality of particles comprising a steroidal anti-inflammatory agent, for example but not limited to, dexamethasone, and a bioerodible polymer, for example but not limited to, a polylactic acid polyglycolic acid (PLGA) copolymer. The plurality of particles, when implanted in an eye, preferably delivers the therapeutic agent to the eye, for example, to the vitreous of the eye, in an amount sufficient to reach a concentration equivalent to at least about 0.05 µg/ml dexamethasone within about 48 hours and maintain a concentration equivalent to at least about 0.03 µg/ml dexamethasone for at least about three weeks. In another embodiment of the invention, the implant preferably delivers the agent to the vitreous in an amount sufficient to reach a concentration equivalent to at least about 0.2 µg/ml dexamethasone within about 6 hours and maintains a concentration equivalent to at least about 0.01 µg/ml dexamethasone for at least about three weeks.

"A concentration equivalent to dexamethasone", as used herein, refers to the concentration of a steroidal anti-inflammatory agent necessary to have approximately the same efficacy in vivo as a particular dose of dexamethasone. For example, hydrocortisone is approximately twenty-five fold less potent than dexamethasone, and thus a 25 mg dose of hydrocortisone would be equivalent to a 1 mg dose of dexamethasone. One of ordinary skill in the art would be able to determine the concentration equivalent to dexamethasone for a particular steroidal anti-inflammatory agent from one of several standard tests known in the art. Relative potencies of selected corticosteroids may be found, for example, in Gilman, A. G., et al., eds. (1990). *Goodman and Gilman's: The Pharmacological Basis of Therapeutics.* 8th Edition, Pergamon Press: New York, p. 1447, which is incorporated herein by this specific reference.

In other embodiments, the implant delivers the agent to the vitreous in an amount sufficient to reach a concentration equivalent to at least about 0.3 µg/ml, or at least about 0.5 µg/ml, or at least about 0.75 µg/ml, or at least about 1.0 µg/ml, or at least about 2.0 µg/ml dexamethasone within about 4 hours, or within about 6 hours, or within about 8 hours, or within about 10 hours, or within about 24 hours.

A concentration equivalent to at least about 0.01 µg/ml, or at least about 0.02 µg/ml, or at least about 0.03 µg/ml, or at least about 0.05 µg/ml, or at least about 0.07 µg/ml dexamethasone may be maintained for an extended period of time (e.g., at least about three weeks or longer). The preferred concentration levels of therapeutic component or drug in the vitreous may vary according to the inflammatory mediated condition being treated. For example, for treating uveitis, a concentration equivalent of at least about 0.01 to 0.1 µg/ml dexamethasone is preferred.

In one embodiment, the concentration of therapeutic component is maintained for least about four weeks. In other embodiments, the concentration is maintained for at least about five weeks, or at least about six weeks, or at least about seven weeks, or at least about eight weeks, or at least about nine weeks, or at least about 10 weeks, or at least about 12 weeks or longer. The preferred duration of therapeutic component or drug release may be determined by the inflammatory mediated condition being treated. For treating uveitis, a drug release duration of at least about three weeks is preferable, more preferably at least about four weeks. In one embodiment, more than one implant 16 may be sequentially implanted into the vitreous, for example in different locations in the vitreous, in order to maintain therapeutic component or drug concentrations for even longer periods.

The formulation of the implants in accordance with the present invention may vary according to the desired therapeutic component release profile, the particular therapeutic component used, the condition being treated, and the medical history of the patient.

Copolymers of glycolic and lactic acid are of particular interest, where the rate of biodegradation is controlled by the ratio of glycolic to lactic acid. The % of polylactic acid in the polylactic acid polyglycolic acid (PLGA) copolymer can be in a range of about 0% to about 100%, preferably about 15% to about 85%, and more preferably about 35% to about 65%. In a particularly preferred embodiment, a 50/50 PLGA copolymer is used. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries.

Moreover, in embodiments in which the implant comprises a plurality of particles, the particles themselves may be made up of different compositions, one from the other. For example, a single implant may comprise one or more particles comprising a first therapeutic component, and one or more other particles comprising a second therapeutic component that is different from the first therapeutic component. Implants made up of various differently composed particles, in different proportions, can be employed to treat the eye.

In some situations, the implant comprises a plurality of different particles having the same or different therapeutic agent, and the same or different release rates and/or delayed release rates. For example, 2, 3, 4 or more different particles can make up an implant. In this way, in a single administration a course of drug treatment may be achieved, where the pattern of release may be greatly varied. For example, a biphasic or triphasic release profile may be achieved with a single administration of an implant comprising a plurality of substantially uniformly sized microparticles having different compositions and/or the same compositions in different proportions.

Various techniques may be employed to produce the particles making up the implants described and shown herein. Useful techniques include, but are not necessarily limited to, extrusion methods, co-extrusion methods, carver press method, die cutting methods, heat compression, combinations thereof and the like. Techniques for producing the therapeutic component of the particles include solvent-evaporation methods, phase separation methods, interfacial methods and the like.

Generally, implants that are compatible for use in the present assemblies can be formed by a number of known methods, including phase separation methods, interfacial methods, extrusion methods, compression methods, molding methods, injection molding methods, heat press methods and the like. Particular methods used can be chosen, and technique parameters varied, based on desired implant size and drug release characteristics. For implants described herein which comprise a plurality of substantially uniformly sized particles, preferably microspheres, which can be delivered through cannulas corresponding to a 21 gauge needle or smaller, and which therefore have cross-sectional diameters of 0.026 inches or less, or similar cross-sectional areas, microfluidic techniques are useful. Extrusion methods, as well as injection molding, compression molding, and tableting methods, may also be effective to achieve the small cross-sectional diameters or areas required of microspheres.

In manufacturing an assembly according to the invention, the implant is loaded in the cannula having the sleeve attached thereto, and the distal closure element and the proximal closure element are used to close the distal opening and the proximal opening respectively. The loaded, closed assembly may then be sterilized using appropriate methods, such as gamma or beta radiation and the like. Inscriptions or indicia located on the sleeve or cannula can include the appropriate information relative to particular implant loaded. Given this interchangeability, unique apparatus for the delivery of selected implants can be easily identified and utilized by providing the particular labeled assembly for the selected implant.

When the assemblies are assembled, it may be further desirable that the implant be positioned just proximal of the opening at the cannula tip. In this fashion, the introduction of air into the eye can be avoided when the implant is ejected, as could otherwise occur were the implant located further within the cannula lumen and an air bubble or air pocket allowed to exist between the cannula tip and the implant and ejection of the implant were to force the air bubble or air pocket into the eye. One method to accomplish this is to load the implant distally into the cannula followed by a holding element located proximal of the implant. The holding element may comprise a suitable structure, for example a detent or berm in the cannula lumen, that maintains the distal position of the implant while allowing fluid from the syringe to bypass the holding element and drive the implant forward during an implant procedure.

To guard against inadvertent premature release of the implant, the cannula can have a slight bend incorporated into the tip such that enough friction exists between the inner wall of the cannula and the implant to hold the implant in place, but at the same time, the frictional force is easily overcome by action of the plunger to eject the implant upon actuation of the apparatus.

Other cannula designs can likewise achieve the desired effect of avoiding the introduction of air into the eye upon ejection of the implant. For example, the implant can be positioned proximally of the cannula tip but with sufficient tolerance between the implant and cannula wall to provide for air exhaust past the implant as it is moved through the cannula. Adequate tolerances are those that retain air in front of the implant at close to ambient pressure as the implant is moved along the cannula. Because fluid pressure within the eye is typically slightly positive relative to ambient pressure, air at ambient pressure will not enter the eye.

As can be appreciated, an apparatus according to the invention that is provided loaded with the desired implant is of great benefit to the physician user. Such apparatus can be provided sterile packaged for a single use application. The user need not ever handle the implant itself. Further, when the apparatus is configured to deliver a micro-implant, the apparatus provides a self-sealing method for delivery, as previously discussed. This has enormous benefit to the physician and patient in that the entire implant procedure can safely, easily, and economically be performed in a physician's office, without the need for more costly surgical support currently required for implant delivery.

Thus, in an exemplary embodiment, the present invention provides a narrow gauge, polymer-based, drug delivery system suitable for intraocular injection. At approximately 0.015 inches in diameter, the ocular implants of the assemblies are typically too brittle and fragile for use in a standard delivery needle or device. However, these implants can be relatively easily placed into the cannulas of the present assemblies which often have dimensions equivalent to a 25 gauge, ultra-thin walled needle or smaller. When attached to a syringe containing a viscous pushing fluid, for example, sodium hyaluronate gel, the assemblies can inject the implants precisely at the required intraocular location. Further, the present assemblies can be safely stored for long periods of time. The assemblies can be sterilized using irradiation, for example, beta or gamma irradiation, and require no additional excipients to seal the implant. While in the assemblies, the implants are protected from light, moisture and microbial contamination. Immediately before injection of the implant from the assembly, the protective closure elements are easily removed from the cannula and the cannula is attached to a syringe containing the pushing fluid.

The following Examples set forth experiments and/or exemplify features of the present invention and are not intended to limit the scope of the present invention.

Example 1

Dexamethasone-Containing Microspheres in a Pre-Loaded Assembly

Microspheres are provided comprising 40% by weight of poly-d, l-lactide-co-glycolide copolymer (Boehringer-Ingleheim 752H) and 60% by weight of dexamethasone, and having uniform diameters of 280±5 µm. Each microsphere has about 0.0083 mg dexamethasone. A cannula having the dimensions of a thin-walled 25 gauge needle (i.d.=0.3 mm) is filled with about 85 of these microspheres, in a side-by-side array, to reach a total drug content of about 0.7 mg. The total length of loaded microspheres in the cannula is about 23.8 mm, compared to 15.8 mm of a thermally extruded rod with a 280 µm diameter and 0.7 mg dexamethasone. The cannula is sealed with closure elements located covering the distal and proximal end openings of the needle to form an assembly that will be later used with a barrel and plunger actuator mechanism to inject the microspheres into an eye without the use of a carrier medium.

Example 2

Dexamethasone-Containing Microspheres and Rod-Shaped Particles Having Different Release Rates in a Pre-Loaded Assembly In batch 1, microspheres are provided comprising 40% by weight poly-d, l-lactide-co-glycolide copolymer (Boehringer-Ingleheim 752H) and 60% by weight dexamethasone, and having uniform diameters of 280±5 µm. Each microsphere has about 0.0083 mg dexamethasone. Separately, in batch 2, extruded rod-shaped particles are provided comprising 40% by weight poly-d, l-lactide (Boehringer-Ingleheim 203S) and 60% by weight dexamethasone, each rod-shaped particle having a length of about 2 mm and a diameter of 280±5 µm. Each rod-shaped particle contains about 0.058 mg dexamethasone. An assembly in accordance with the invention as described herein is provided including a cannula having the dimensions of a thin-walled 25-g needle (i.d.=0.3 mm). The cannula is filled with about 42 microspheres from batch 1 and 6 rod shaped particles from batch 2 to reach a total drug content of about 0.7 mg. Total length of loaded microspheres and rod shaped particles in the cannula is about 23.8 mm, compared to 15.8 mm of a thermally extruded rod with a 280 µm diameter and 0.7 mg dexamethasone. The cannula is sealed with closure elements located covering the distal and proximal end openings of the needle to form an assembly that will be later used with a barrel and plunger actuator mechanism to inject the microspheres into an eye without the use of a carrier medium.

Example 3

Treatment of Glaucoma Using an Implant Made Up of Bimatoprost-Containing Microspheres and Cyclosporine-Containing Microspheres A 72 year old female suffering from glaucoma in both eyes receives an intraocular implant in each of both eyes using assemblies in accordance with the invention. Each assembly includes a cannula having dimensions equivalent to a 25 gauge needle. The cannula contains an implant made up of 100 microspheres, each microsphere having a diameter of about 500 μm. 90 of the microspheres contain bimatoprost and poly-d, l-lactide-co-glycolide copolymer, and 10 of the microspheres contain a cyclosporine and poly-d, l-lactide-co-glycolide copolymer. The proximal and distal end openings of the cannula are sealed with proximal and distal closure elements, respectively, as described elsewhere herein. After removing the proximal and distal closure elements, the cannula is coupled to a syringe containing a suitable amount of an aqueous-based pushing gel. Each eye then receives an implant containing about 500 mg of bimatoprost and about 0.0028 mg of cyclosporine. The implant is delivered into the vitreous of each eye using the syringe coupled to the cannula and the pushing gel.

In about two days, the patient reports a substantial reduction in ocular discomfort. Examination reveals that the intraocular pressure has decreased; the average intraocular pressure measured at 8:00 AM has decreased from 28 mm Hg to 14.3 mm Hg. The patient is monitored monthly for about 6 months. Intraocular pressure levels remain below 15 mm Hg for the next six months

Example 4

Manufacture and Extended Storage of Bimatoprost/Polymer Intraocular Implant-Containing Assemblies Bimatoprost is combined with a biodegradable polymer composition in a mortar. The combination is mixed with a shaker for about 15 minutes. The resulting powder blend is scraped off the wall of the mortar and is then remixed for an additional 15 minutes. The mixed powder blend is then heated to a semi-molten state at a specified temperature for a total of 30 minutes, forming a polymer/drug melt.

The polymer/drug melt is pelletized using a 9 gauge polytetrafluoroethylene (PTFE) tubing. The pellets are melted and extruded at a specified core extrusion temperature to form very thin filaments having maximum diameters of about 0.015 inches. The filaments are then cut into individual implants, each having a length of about 6 mm.

One of the implants is loaded into a 25-gauge cannula having a sleeve suitable for coupling a distal end of the cannula to a standard syringe and a needle length of about 15 cm. Silicone polymer closure elements are coupled to the proximal and distal ends of the cannula. The assembly made up of the cannula, sleeve, implant and closure elements is sealed and sterilized by irradiating the entire assembly with gamma radiation. The sterilized assembly is then appropriately labeled, packaged and stored in a cool dry location. When the assembly is opened and examined a year later, it is observed that the implant has not eroded, degraded or otherwise chemically or physically changed in any significant way from when the assembly was originally produced.

Example 5

Bimatoprost/Polymer Implants Used to Treat Glaucoma

A 72 year old female is suffering from glaucoma in both eyes. A physician selects two packages, each containing an assembly containing a bimatoprost/polymer implant, the assembly having been produced six months earlier as described in Example 4. The physician treats each eye by opening one of the packages, removing the closure elements from the proximal and distal ends of the cannula, coupling the pre-loaded cannula to a syringe containing a suitable pushing fluid, and injecting the implant into the vitreous of the eye. In about two days, the patient reports a substantial relief in ocular comfort. Healing of the injection site appears to be complete. Further examination reveals that the intraocular pressure has decreased, the average intraocular pressure measured at 8:00 AM has decreased from 28 mm Hg to 14.3 mm Hg. The patient is monitored monthly for about 6 months. Intraocular pressure levels remain below 15 mm Hg for six months, and the patient reports reduced ocular discomfort.

Example 6

Dexamethasone/PLGA Implants Used to Treat Macular Degeneration

A 70 year old female patient complains of blind spots in her vision. Upon examination, the physician diagnoses her with the wet form of macular degeneration. Upon examination of her eyes, it is found that blood vessels have grown beneath the retina of each eye and are leaking blood and fluid which are causing the blind spots. On the day of scheduled treatment, the physician selects a pre-filled assembly in accordance with the invention from a supply of such pre-filled assemblies. Each selected assembly is contained in a sterile packaging and appropriately labeled as containing an implant in the form of 80 bioerodible microspheres each containing dexamethasone (70 percent by weight) distributed in a polylactic acid polyglycolic acid (PLGA) copolymer (30 percent by weight). The physician carefully removes the proximal closure element from one end of the cannula and secures the sleeve of the assembly to a syringe containing an appropriate amount of sodium hyaluronate gel. The physician removes the distal closure element from the distal end of the cannula and positions the distal end of the cannula in the vitreous of the eye. The physician presses the syringe plunger to cause the gel to push the microspheres into the eye. After three days, the patient is examined and there is found a decrease in the amount of leakage at the back of the eyes. The implants are left to remain in the patient's eyes in order to provide continuous dosing of dexamethasone over the next two months. Vision is improved and further degeneration of vision is prevented.

Example 7

Manufacture of Pre-Loaded Assemblies Containing Triamcinolone Acetonide Suspended in a Sodium Hyaluronate Viscous Medium Assemblies in accordance with the invention are manufactured as follows.

A concentrated triamcinolone acetonide dispersion is made by combining triamcinolone acetonide with water, Vitamin E-TPGS and γ-cyclodextrin. These ingredients are mixed to disperse the triamcinolone acetonide, and then autoclaved.

Sodium hyaluronate is purchased as a sterile powder. The sterile sodium hyaluronate is dissolved in water to make an aqueous concentrate. The concentrated triamcinolone acetonide dispersion is mixed and added as a slurry to the sodium hyaluronate concentrate. Water is added q.s. (quantum sufficit, as much as suffices, in this case as much as is required, to prepare the suspension) and the mixture is mixed until homogenous.

The homogenous mixture is a loose flocculation of triamcinolone acetonide particles suspended in a viscous sodium hyaluronate medium. The homogenous mixture is loaded in unit doses into sterile 25 gauge cannulas which are sealed and packaged as described in Example 4. The packages are sterilized by beta or gamma radiation.

The assemblies are marketed as single dose unit packages that are therapeutically effective in treating macular edema when injected intravitreally into human eyes.

Example 8

Pre-Loaded Assembly with Plugged, Small Diameter Cannula

An alternate embodiment of an ocular implant delivery assembly ("applicator") can comprise a bioerodible polymeric plug to keep the implant in the needle (that is in the cannula) of the applicator without any need to secure the implant with a sleeve or O-ring. This can be accomplished by putting the bioerodible polymeric plug into the applicator cannula. The cannula is a 25 gauge needle cannula. Thus, the implant is loaded in the cannula and about 10-30 ul of a suitable lubricant such as HPMC (hydroxypropyl methyl cellulose) is then applied to just the distal end of the cannula (that is to block just the lumen at the distal end of the cannula), or preferably the biodegradable plug material is applied so as to block both proximal and distal end openings of the pre-loaded (with the implant) cannula, that is both distal and proximal to the implant in the lumen of the cannula. A cellulose lubricant such as HPMC dries over night as a film and acts to decrease the internal diameter of both end openings of the cannula thereby preventing the implant from falling out of the cannula. The bioerodible polymer plug material can be any suitable material which can act to temporarily plug one or both ends of the lumen (distal alone or both distal and proximal to the implant in the lumen of the cannula). The plug serves the temporary purpose of retaining the implant securely in the lumen until the plunger is advanced, and the plug is thereby broken (film plug) or advanced along with the implant into the ocular site of administration of the implant.

When ready for use, a needle assembly which comprises the blocked HPMC blocked cannula is placed onto a syringe filled with either saline, or a more viscous solution like hyaluronic acid or HPMC, and the polymeric seals are easily broken when the plunger of the syringe is advanced. Having a sleeveless needle on the applicator allows the use of ultra-thin wall needles. 25G Popper needles which have an internal diameter of 0.015 inch may be used. This embodiment provides a sleeveless system which permits use of thin-wall needles to thereby significantly reduce the size of the hole in the eye upon use of the applicator and still maintain implants that have reasonable diameters. A sleeveless needle also allows for deeper entry into the vitreous or sub-Tenon's space since the somewhat obstructive sleeve is not present.

Example 9

Pre-Loaded Assembly with Capped, Small Diameter Cannula

A further alternate embodiment of an ocular implant delivery assembly can comprise a polymeric cap to keep the implant in the needle or cannula of the assembly without any need to secure the implant with a sleeve or O-ring. This can be accomplished by putting a polymeric cap, for example and without limitation, a flexible or soft, substantially clear silicone polymeric cap, onto the distal end of the cannula. The cannula is a 25 gauge needle. The cap is substantially as shown in FIGS. 10 to 14, and described elsewhere herein. The cap, prior to being placed on the distal end of the cannula, is a substantially solid soft silicone polymeric disc. Thus, substantially no structure, such as a partial bore, is included in the cap prior to the cap being placed on the distal end of the cannula. The cap covers the entire distal end opening of the cannula. The cap also has markings every 0.25 mm radially outwardly from the cannula which provides a scale of the distance between each marking and the cannula.

After the implant is placed into the lumen of the cannula, the cap is placed over the distal end opening and distal end of the cannula so that the distal end opening of the cannula is within the silicone polymeric disc. In this manner, not only is the implant prevented from passing through the distal end opening of the cannula but, in addition, the distal end opening of the cannula is sealed so that no fluid can enter the lumen of the cannula through the distal end opening or exit the lumen through the distal end opening.

In addition, either a removable proximal closure element and/or a proximal plug can be placed near the proximal end opening of the cannula to seal the proximal end opening prior to use of the assembly.

In use, the cannula, for example with the proximal plug and/or removable proximal closure element removed, is secured to a syringe or push-rod device. The silicone polymeric cap remains in place. The silicone polymeric cap and exposed portion of the cannula are dipped in normal saline solution to lubricate the cannula and cap. The silicone polymeric cap is placed in contact with a surface of an eye, for example, using the scale noted above to determine the desired implantation location, such as by placing the tip of the cannula at a specific distance from the limbus of the eye, into which the implant is to be placed. Because the cap is clear, the operator can see the cannula tip through the cap and can verify that the cannula tip is at the desired implantation location. The cannula is urged distally so that it passes through the cap and into the eye. As the cannula passes through the cap, substantially no silicone polymeric material passes into the lumen of the cannula or into the eye. The cannula is moved further into the eye until it is located at the target area within the eye in which the implant is to be placed. This distal movement of the cannula into the eye causes the silicone polymeric cap to move proximally along the cannula toward the syringe device or push-rod device. The operator performing the procedure is provided with a visualization of how far the cannula has been placed in the eye based on the distance between the cap and the syringe device or push-rod device.

Once the distal end and distal end opening of the cannula are at the target location within the eye, the syringe device or push-rod device is activated to urge the implant in the lumen of the cannula forward or distally out of the lumen and into the eye. After implantation of the implant, the cannula is removed from the eye and the procedure is completed.

A number of publications and patents have been cited hereinabove. All of the cited publications and patents are hereby incorporated by reference in their entireties.

While this invention has been described with respect to various specific examples and embodiments, it is to be understood that the invention is not limited thereto and that it can be variously practiced within the scope of the following claims.

What is claimed is:

1. An ocular implant delivery assembly comprising:
   (a) a cannula having an outer wall, a proximal end, a proximal end opening, a distal end, a distal end opening, and a lumen extending through the cannula;
   (b) an ocular implant sized and structured for implantation in an eye, the ocular implant comprising polylactic acid, polyglycolic acid, and bimatoprost;
   (c) a distal closure element having a bioerodible polymeric plug adapted to be passed into the eye, located in the lumen and closing the distal end opening of the cannula;
   (d) a proximal closure element closing the proximal end opening of the cannula; and
   (e) a clear, circular cap having a closed distal end, being in contact with the outer wall of the cannula, and covering the distal end and the distal end opening of the cannula, the cap being structured (i) to allow the distal end and the distal end opening of the cannula to pass through the cap as the cannula is passed into an eye and ii) to move proximally along the cannula as the cannula is passed into the eye;
   wherein the proximal end of the cannula is adapted to receive a syringe assembly, and the ocular implant is located in the lumen between the distal closure element and the proximal closure element, and
   wherein the bioerodible polymeric plug comprises a material selected from the group consisting of cellulose and cellulosic derivatives.

2. The assembly of claim 1 wherein the cannula is a 25 gauge or higher gauge syringe needle, and wherein the bioerodible polymeric plug comprises a cellulosic derivative.

3. The assembly of claim 2, wherein the cellulosic derivative is hydroxypropyl methyl cellulose (HPMC).

4. The assembly of claim 1 wherein the proximal closure element comprises a bioerodible proximal plug.

5. The assembly of claim 1 wherein the ocular implant comprises a plurality of particles.

6. The assembly of claim 5 wherein the plurality of particles includes a number of particles in a range of about 5 to about 200.

7. The assembly of claim 5 wherein the plurality of particles includes particles having different compositions.

8. The assembly of claim 5 wherein the plurality of particles comprise particles having different release rates.

9. The assembly of claim 1 wherein the ocular implant comprises a plurality of particles in a one-by-one array along a length of the lumen.

10. The assembly of claim 1 wherein the ocular implant comprises a plurality of particles selected from the group consisting of spheres, rods, filaments, plaques and combinations thereof.

11. The assembly of claim 1 wherein the ocular implant comprises a plurality of substantially uniformly sized microspheres.

12. The assembly of claim 1 wherein the lumen has a diameter of less than about 350 microns.

13. The assembly of claim 1 further comprising a carrier medium located in the cannula.

14. The assembly of claim 13 wherein the ocular implant comprises a plurality of particles in contact with the carrier medium in the lumen.

15. The assembly of claim 1 wherein substantially no liquid material is present in the lumen with the ocular implant.

16. The assembly of claim 1 which further comprises a syringe assembly coupled to the proximal end of the cannula and effective, when activated, in passing the ocular implant out of the cannula.

17. The assembly of claim 1 which further comprises a push-rod assembly coupled to the cannula and effective, when activated, in passing the ocular implant out of the distal end opening of the cannula.

18. A method of implanting an ocular implant into an eye comprising: providing an ocular implant delivery assembly according to claim 17,
   passing at least a portion of the cannula into the eye; and
   applying a force to urge the implant distally, thereby placing the implant in the eye.

19. An ocular implant delivery assembly comprising:
   (a) a cannula having an outer wall, a proximal end, a distal end, and a lumen extending through the cannula, the cannula having an outer diameter no larger than a 25 gauge syringe needle;
   (b) an ocular implant sized and structured for implantation in an eye, the ocular implant comprising polylactic acid, polyglycolic acid, a corticosteroid, and being located in the lumen of the cannula;
   (c) a distal bioerodible plug adapted to be passed into the eye, located in the lumen and sealing the distal end of the cannula;
   (d) a proximal bioerodible plug located in the lumen and sealing the proximal end opening of the cannula;
   (e) a syringe assembly coupled to the proximal end of the cannula; and
   (f) a clear, circular cap having a closed distal end, being in contact with the outer wall of the cannula, and covering the distal end and the distal end opening of the cannula, the cap being structured (i) to allow the distal end and the distal end opening of the cannula to pass through the cap as the cannula is passed into an eye and ii) to move proximally along the cannula as the cannula is passed into the eye;
   wherein the ocular implant is located in the lumen between the proximal bioerodible plug and the distal bioerodible plug, and
   wherein each of the proximal bioerodible plug and the distal bioerodible plug comprise a polymeric material selected from the group consisting of cellulose and cellulosic derivatives.

20. The assembly of claim 19 wherein the polymeric material is hydroxypropyl methyl cellulose (HPMC).

* * * * *